US007638680B2

(12) United States Patent
Carman

(10) Patent No.: US 7,638,680 B2
(45) Date of Patent: *Dec. 29, 2009

(54) METHODS FOR STABILIZING AND CONTROLLING APOMIXIS

(75) Inventor: John G. Carman, Smithfield, UT (US)

(73) Assignee: Utah State University, North Logan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/772,243

(22) Filed: Feb. 6, 2004

(65) Prior Publication Data

US 2004/0216193 A1  Oct. 28, 2004

Related U.S. Application Data

(63) Continuation-in-part of application No. 09/744,614, filed as application No. PCT/US00/29905 on Oct. 30, 2000, now abandoned, and a continuation-in-part of application No. 09/576,623, filed on May 23, 2000, now Pat. No. 6,750,376, which is a continuation of application No. 09/018,875, filed on Feb. 5, 1998, now abandoned.

(60) Provisional application No. 60/162,626, filed on Oct. 29, 1999, provisional application No. 60/037,211, filed on Feb. 5, 1997.

(51) Int. Cl.
*A01H 1/00* (2006.01)
(52) U.S. Cl. ........................................ 800/260; 800/271
(58) Field of Classification Search ................ 800/260, 800/266, 269, 270, 271, 276, 298
See application file for complete search history.

(56) References Cited

U.S. PATENT DOCUMENTS

| 5,710,367 | A | 1/1998 | Kindiger et al. ............. 800/200 |
| 5,767,374 | A | 6/1998 | De Greef et al. ............. 800/205 |
| 5,811,636 | A | 9/1998 | Hanna et al. ................. 800/200 |
| 6,750,376 | B1 * | 6/2004 | Carman ....................... 800/260 |
| 2004/0168216 | A1 | 8/2004 | Carman ....................... 800/287 |

FOREIGN PATENT DOCUMENTS

| WO | WO 98/28431 | 7/1998 |
| WO | WO/01/32001 | 10/2001 |

OTHER PUBLICATIONS

Bashaw. 1980. Apomixis and its application in crop improvement. In Hybridization of crop plants. pp. 45-63.*
Koltunow et al. 2003. Annu. Rev. Plant Biol. 54: 547-574.*
Savidan. 2000. Plant Breeding Reviews 18: 13-86.*
Asker. 1979. Hereditas 91: 231-240.*
van Dijk et al. 2000. Trends in Plant Science 5(2): 81-84.*
Grimanelli et al. 2001. Trends in Genetics 17(10): 597-604.*
de Wet et al. 1970. Caryologia 23: 183-187.*
Dewey. 1977. Crop Sci. 17: 106-111.*
Barnabas et al. 1991. Theor. Appl. Genet. 81: 675-678.*
Lutts et al. 1994. Euphytica 78: 19-25.*
Bashaw. 1980. Apomixis in crop improvement. In Hybridization of crop plants. pp. 57-62.*
Savidan. 1982. Crop Sci. 22: 467-469.*
Dujardin et al. 1988. Euphytica 38: 229-235.*
International Preliminary Examination Report for PCT/US2000/029905 dated Feb. 6, 2002 (4 pages).
Savidan, "Progress in research on apomixis and its transfer to major grain crops", In Reproductive Biology and Plant Breeding, pp. 269-279 (1992).
Stuber, "Mating designs, field nursery layouts, and breeding records", In Hybridization of Crop Plants, p. 100 (1980).
Yuan, L. P., "Progress of two-line system in hybrid rice breeding", New Frontiers in Rice Research, K. Muralidhoran, EA Siddig (eds), Hyderabad, India: Directorate of Rice Research, pp. 86-90 (1993).
Asker and Jerling, Apomixis in Plants, p. 114. 1992.
Asker and Jerling, Apomixis in Plants, pp. 81-107, 241-283. 1992.
Asker, S.E. et al., "Apomixis in Plants," CRC Press, Inc., Boca Raton, Florida, 1992.
Barcaccia et al. Comparison between isozyme and RAPD analyses to screen aberrant plants in *Poa pratensis* L. progenies, in Apomixis Newsletter, 7:29-30. 1994.
Barcaccia et al., Environmental Influences on the Frequency and Viability of Meiotic and Apomeiotic Cells of a Diploid Mutant of Alfalfa. Crop Science. vol. 37, pp. 70-76. 1997.

(Continued)

*Primary Examiner*—Anne Marie Grunberg
*Assistant Examiner*—Keith O. Robinson

(57) ABSTRACT

Methods are disclosed for detecting genetic instability for apomixis in angiospermous plant, and for enhancing, genetically stabilizing, and controlling apomixis expression in such plants. Enhanced expression, stabilization, and control are achieved by converting a facultative apomict to obligate apomixis. Enhanced expression of apomixis is further achieved by increasing frequencies of unreduced egg formation and/or parthenogenesis. Genetic stabilization of apomixis is alternatively achieved by conferring mechanisms to a facultative apomict that, during facultative sexual seed formation, prevent the segregational loss of unique alleles at multiple loci, which cause apomixis, such that progeny produced sexually from the facultative apomict inherit the unique allelic combinations required to maintain apomixis. The disclosed methods are used in various combinations to produce apomictic plants that possess improved yield, quality, and/or seed production characteristics.

33 Claims, 9 Drawing Sheets

OTHER PUBLICATIONS

Bashaw et al., Apomictic grasses. In: Principles of Cultivar Development vol. 2, Fehr (ed.), Macmillan Publishing Company, New York, pp. 40-82. 1987.

Bashaw, Apomixis and its Application in Crop Improvement. Hybridization of Crop Plants, Fehr et al. (eds.), American Society of Agronomy and Crop Science Society of America, Madison, pp. 45-63. 1980.

Bates et al., 1974, Wide Crossess. In: Proceedings of World-wide maize improvement in the 70's and the role of CIMMT, Apr. 22-26 El Batan, Mexico. 7 pp. CIMMT.

Battaglia, R., 1989. The Evolution of the Female Gametophyte of Angiosperms: an Interpretive Key, Annali di Botanica 47:7-144.

Baum et al. Wide Crosses in Cereals. Annu. Rev. Plant Physiol. Plant Mol. Biol., 43:117-43. 1992.

Bayer, R.J., Evolution of Polyploid Agamic Complexes with Examples from *Antennaria* (Asteraceae), Opera Botanica 132:53-65 (1996).

Bell, P.R, Apospory and Apogamy: Implication for Understanding the Plant Life Cycle, International Journal of Plant Sciences 153: S123-S136 (1992).

Bennett, S.T. et al., Spatial Separation of Ancestral Genomes in the Wild Grass Milium montianum Parl., Annals of Botany 70:111-118 (1992).

Carman JG, The evolution of gametophytic apomixis, In Batygina (ed) Embryology of Flowering Plants, vol. 3, The Systems of Reproduction, Russian Acad Sci, St. Petersburg. 230-236. 2000.

Carman JG. Asynchronous expression of duplicate genes in angiosperms may cause apomixis, bispory, tetraspory, and polyembryony. Biol J. Linnean Soc 61: 51-94. 1997.

Carman, Evolution of Apomixis in *Antennaria* (Asteraceae): A Model Involving Hybrid Origins and Karyotypic Stabilization, presented at Plant & Animal Genome XI, The International Conference on the Status of Plant & Animal Genome Research. Town & Country Hotel, San Diego, California. Jan. 11-15, 2003.

Carman, J.G., Aposporous Apomixis in *Schizachyrium* (Poaceae:Androppogoneae), Crop Science 2:1252-1255 (1982).

Carman, J.G., Comparative Histology of Cell Walls During Meiotic and Apomeiotic Megasporogeny in Two Hexaploid Australian Elymus species, Crop Science 31:1526-1532 (1991).

Carman, J.G., Gametophytic Angiosperm Apomicts and the Occurrence of Polyspory and Polyembrony Among Their Relatives, Apomixis Newsletter 8:39-53 (1995).

Carman, J.G., Phylogeny of Apomictic, Polysporic and Polyembroynic Angiosperms: Evolutionary and Regulatory Implications, Abstract of a paper presented at the international conference, Harnessing Apomixis, Sep. 25-27, College Station, Texas (1995).

Crane, C.F. et al., Mechanismsm of Apomixis in *Elymus rectisetus* from Eastern Australia and New Zealand, American Journal of Botany, vol. 74, pp. 477-496, 1987.

de Wet et al. 1970. Stable triploid hybrids among Zea-Tripsacum-Zea backcross populations. Caryologia 23:183-187.

De Wet, J.M.J. et al., Gametophytic Apomixis and Evolution in Plants, Taxon 23:689-697 (1974).

Ellerstrom et al., 1977. Sterility and apomictic embryo-sac formation in Raphanobrassica. Hereditas 87:107-120.

Ellerstrom et al., 1983. Apomictic progeny from Raphanobrassica. Hereditas 99:315.

Eshed et al., 1996. Less-than-epistatic interactions of quantitative trait loci in tomato. Genetics 143:1807-1817.

Evans et al. Environmental Control of Reproduction in *Themeda australis*, Aust. J. Bot., 17:375-89. 1969.

Garcia et al., 2000. Genetic variation in the progeny of maize/Tripsacum hybrids. Maize Genet. Coop. Newsletter 74:40-41.

Grimanelli et al, Mapping diplosporous apomixis in tetraploid *Tripsacum*: one gene or several genes, Heredity 80:33-39. 1998.

Hanna et al., Apomixis: Its identification and use in plant breeding. Crop Science. vol. 27, pp. 1136-1139. 1987.

Holm et al. 1996. Sexuality and no apomixis found in crossing experiments with diploid *Potentilla argentea*. Hereditas 125:77-82.

Hovin et al., Apomixis in Kentucky bluegrass. Crop Science. vol. 16, pp. 635-638. 1976.

Hussey et al. Influence of photoperiod on the frequency of sexual embryo sacs in facultative apomictic buffelgrass, Euphytica 54:141-145. 1991.

Jankun, A. et al., Apomixis at the Diplois Level in Sorbus Eximia (Embryological Studies in Sorbus 3), P. Praha 60:193-213 (1988).

Jefferson and Bicknell, The potential impacts of apomixis: a molecular genetics approach, in *The Impact of Plant Molecular Genetics*, Birkhauser, Boston, pp. 88-89, 94, 98). 1996.

Johri, et al., Comparative Embryology of Angiosperms, vol. 1, pp. 1-4, 29-41, and 84-94, 1992.

Knox, R.B. et al., Experimental Control of Apsorous Apomixis in a Grass of the Andropogoneae, Botanisk Notiser 116:127-141 (1963).

Knox, R.B., Apomixis: Seasonal and Population Differences in a Grass, Science 157:325-326 (1967).

Koltunow, A.M. et al., Apomixis: Molecular Strategies for the Generation of Genetically Identical Seeds Without Fertilization, *Plant Physiology*, vol. 108, pp. 1345-1352 (1998).

Kraft et al. 2000. Linkage disequilibrium and fingerprinting in sugarbeet. Theor. Appl. Genet. 101:323-326.

Kultunow et al. Apomixis: molecular strategies for the generation of genetically identical seeds without fertilization, Plant Physiol 108: 1345-1352. 1995.

Leblanc et al. Detection of the apomictic mode of reproduction in maize-*Tripsacum* hybrids using maize RFLP markers, Theor Appl Genet 90: 1198-1203. 1995.

Leblanc, O. et al., Megasporogenesis and Megagametogenesis in Several Tripsacum species (Poaceae), American Journal of Botany 82:57-63 (1995).

Leblanc, O. et al., Timing of Megasporogenesis in Tripsacum species (Poaceae) as Related to the Control of Apomisix and Sexuality, Polish Botanical Studies *:75-81 (1994).

Liu et al. Hybrids and backcross progenies between wheat (*Triticum aestivum* L.) And apomictic Australian wheatgrass [*Elymus rectisetus* (Nees in Lehm.) A. Löve & Connor]: karyotypic and genomic analyses, Theor Appl Genet, 89:599-605. 1994.

Marshall, D.R., et al., The Evolution of Apomixis, Heredity 47:1-15 (1981).

Mogie, M. A Model for the Evolution and Control of Generative Apomisix, Biological Journal of the Linnean Society 35:127-153 (1988).

Mogie, The Evolution of Asexual Reproduction in Plants, 139-196. 1992.

Mujeeb-Kazi, A., Apomictic Progeny Derived from Intergeneric Hordium-Triticum Hybrids, The Journal of Heredity:72-284-285 (1981).

Mujeeb-Kazi, A., Apomixis in Trigeneric Hybrids of *Triticum aestivum/Leymus racemosa/Thinopynum elongatum*, Cytologia 61:15-18 (1996).

Naumova et al., Apomixis in plants: structural and functional aspects of diplospory in *Poa nemoralis* and *P. palustris*, Protoplasma 208:186-195, 1995.

Naumova, T.N. et al., Quantitative Analysis of Aposporous Parthenogenesis in *Poa pratensis* Genotypes, Acta Botanica Neerlandica 42:299-312 (1993).

Naumova, T.N. et al., Ultrastructural Characteristics of Apospory in *Panicum maximum*, Sexual Plant Reproduction 8:197-204 (1995).

Nogler, G.A., Genetics of Gametophytic Apomixis—A Historial Sketch, Polish Botanical Studies 8:5-11 (1994).

Nordborg, B., Embryological Studies in the Sanguisorba Minor Complex (Rosaceae), Botaniska Notiser 120:109-119 (1967).

Ozians-Akins, P., et al., Transmissions of the Apomictic Mode of Reproduction in Pennisetum: Co-Inheritance of the Trait and Molecular Markers, Theoretical and Applied Genetics 85:632-638 (1993).

Ozias-Akins et al. Tight clustering and hemizygosity of apomixis-linked molecular markers in *Pennisetum squamulatum* implies genetic control of apospory by a divergent locus that may have no allelic form in sexual genotypes, Proc Natl Acad Sci 95: 5127-5132, 1998.

Ozias-Akins, Characterization of the Genomic Region Associated with the Transmission of Apomixis in *Pennisetum* and *Cenchrus*, presented at Plant & Animal Genome XI, The International Conference on the Status of Plant & Animal Genome Research. Town & Country Hotel, San Diego, California. Jan. 11-15, 2003.

Peacock, J., Genetic Enginering and Mutagenesis for Apomixis in Rice, In. Wilson KJ, ed., Proceedings of the International Workshop of Apomixis in Rice, Changsha, China. New York: Rockefeller Foundation 11-22 (1993).

Peel, M.D. et al., Megasporocyte Callose in Apomictic Buffelgrass, Kentucky Bluegrass, *Pennisetum squamulatum* Fresen, *Tripsacum* L., and Weeping Lovegrass, Crop Science, vol. 37, No. 3, 1997.

Peel, M.D. et al., Meiotic Anomalies in Hybrids Between Wheat and Apomictic *Elymus rectisetus* (Nees in Lehm.) A. Love & Connor, Crop Sci. 37:717-723 (1997).

Poehlman, Breeding Field Crops, 3$^{rd}$ Ed., pp. 164-165, 332-339. 1987.

Purnhauser et al., 1993. A method for crossing non-synchronously flowering parents in wheat, using cold storage of the female parent. Cereal Res. Comm. 21(2-3):175-179.

Quarin, Seasonal changes in the incidence of apomixis of iploid, triploid, and tetraploid plants of *Paspalum cromyorrhizon*. Euphytica. vol. 35, pp. 515-522. (Abstract only) 1986.

Ramula et al. Apomixis for crop improvement, Protoplasma 208: 196-205 (see Abstract and Conclusions). 1999.

Ramulu et al., Apomixis for crop improvement. Protoplasma. vol. 208, pp. 196-205. 1999.

Salisbury et al. Plant Physiology, 4$^{th}$ Ed., pp. 504-514. 1992.

Saran et al. 1976. Environmental control of reproduction in *Dichanthium intermedium*. J. Cytol. Genet. 11:22-28.

Sharbel et al. Genome-Wide Genetic Variability and DNA Sequence Divergence along an Aneuploid Chromosome Associated with Apomixis in the *Arabis holboellii* Complex, presented at Plant & Animal Genome XI, The International Conference on the Status of Plant & Animal Genome Research. Town & Country Hotel, San Diego, California. Jan. 11-15, 2003.

Sherman, R.A. et al., Apomixis in Diploid X Triploid *Tripsacum dactyloides* hybrids, Genome 34:528-532 (1991).

Sherwood et al. Inheritance of apospory in buffelgrass, Crop Sci 34:1490-1494. 1994.

That, New developments in hybrid rice. International Rice Commission Newsletter. vol. 42, pp. 28-34. (Abstract only) 1993.

Torabinejad et al. Morphology and genome analyses of interspecific hybrids of *Elymus scabrus*, Génome, 29:150-155. 1987.

Vielle Calzada, J-P et al., Apomixis: the Asexual Revolution, Science 274:1322-1323 (1996).

von Bothmer R. et al., Complex Interspecific Hybridization in Barley (*Hordium vulgare* L. and the Possible Occurrence of Apomixis. Theoretical and Applied Genetics, 76:681-690 (1988).

Zenkteler. In Vitro Fertilization and Wide Hybridization in Higher Plants, Critical Reviews in Plant Sciences, 9: 267-279. 1990.

* cited by examiner

Synthetic Facultative Tripsacum Apomict
*Sexual Development*     *Diplosporous Development*
*Fig. 9*

METHODS FOR STABILIZING AND CONTROLLING APOMIXIS

CROSS-REFERENCE TO RELATED PATENT APPLICATIONS

This application is a continuation-in-part of U.S. application Ser. No. 09/744,614, filed Jan. 26, 2001 now abandoned (which is the National Stage of International Application No. PCT/US00/29905, filed Oct. 30, 2000, which itself claims the benefit of U.S. Provisional Application No. 60/162,626, filed on Oct. 29, 1999), and of U.S. application Ser. No. 09/576,623, filed May 23, 2000, now issued as U.S. Pat. No. 6,750,376, (which is a continuation of U.S. application Ser. No. 09/018,875, filed Feb. 5, 1998, now abandoned, which itself claims the benefit of U.S. Provisional Application No. 60/037,211, filed Feb. 5, 1997), the disclosures of each of which are expressly incorporated herein by reference thereto.

BACKGROUND OF THE INVENTION

This invention relates to the fixation of hybrid vigor and other traits through apomixis (asexual seed formation) in flowering plants (angiosperms). More particularly, it provides methods for "stabilizing" apomixis in natural or man-made facultative apomicts (plants capable of sexual and apomictic reproduction) such that sexually-derived progeny, which are occasionally produced facultatively from such apomictic plants, tend to be apomictic like the mother plant, though otherwise genetically recombined, instead of being sexual revertants. It also provides methods for "controlling" apomixis, in natural or synthetic apomicts, such that such apomicts express obligate apomixis (no capacity for sexual seed formation), obligate apomixis except when induced to be facultatively apomictic, or facultative apomixis except when induced to be obligately apomictic. This invention uses genetic, cytogenetic, and molecular modifications to prevent genetic recombination among loci critical to the expression of apomixis (stabilization of apomixis) and controls the percentage of seeds that are derived apomictically by controlling frequency of sexually-derived seeds in natural or synthetic facultative apomicts (control of apomixis).

The types of apomixis referred to in the present patent application cause asexual seed formation. Accordingly, seeds of apomictic plants contain embryos that are genetic clones of the mother plant. Such forms of apomixis comprise adventitious embryony and gametophytic apomixis (referred to hereinafter as apomixis), which is commonly divided into apospory and diplospory. S. E. Asker & L. Jerling, Apomixis in Plants (CRC Press 1992) (hereinafter, "Asker & Jerling").

Developmental signals responsible for apomixis preempt megasporogenesis by inducing precocious embryo sac formation from either the megaspore mother cell (MMC) (diplospory) or from somatic nucellar cells (apospory). Fertilization is also preempted by precocious embryony, which often occurs before the stigma is receptive to pollen. Wobble in the intensity of signals responsible for apomixis allows for the facultative expression of sexual reproduction within apomictic plants. Hence, in most apomicts, a certain percentage of seeds produced by a single apomictic plant will form sexually, and this percentage is often influenced by environmental factors. Asker & Jerling. In *Antennaria*-type diplospory, signals for precocious embryo sac formation occur very early, completely preventing meiosis. In *Taraxacum*-type diplospory, signals for embryo sac formation are less precocious and affect the MMC after meiosis has initiated. In *Hieracium*-type apospory, nucellar cells are affected by the precocious and ectopic embryo-sac-inducing signals, and the affected somatic nucellar cells undergo three rounds of endomitosis to produce an 8-nucleate embryo sac. In *Panicum*-type apospory, only two rounds of endomitosis occur, resulting in mature 4-nucleate embryo sacs. In adventitious embryony, embryos form from cells other than the egg, including cells of the nucellus, integument(s), synergids, and antipodals. Asker & Jerling.

Technologies that induce, stabilize, and control the expression of apomixis in crops have the potential of revolutionizing plant breeding and becoming essential to competitive agribusiness worldwide. With such systems, breeders will "clone" highly desirable plants (exhibiting hybrid vigor, transgenic traits, and the like) through the plant's own seed—generation after generation. Yield increases resulting from the fixation of hybrid vigor of inbred crops such as wheat (15%) and rice (35%) will be economically exploited on a large scale for the first time, which will make apomixis of immense commercial value worldwide. Because cloning occurs through seed, apomixis may become the most cost effective plant mechanism for transferring biotechnological and productivity advances to marginal farmland in the developed world and to resource poor farmers in developing nations. Apomixis may become among the most valuable genetic tools for plant breeders in the 21st century. At a recent conference on apomixis, the following conclusion was reached: "The prospect of introducing apomixis into sexual crops presents opportunities so revolutionary as to justify a sustained international scientific effort. If apomixis were generated with a sufficiently high degree of flexibility, the impact on agriculture could be profound in nature and extremely broad in scope." The Bellagio Apomixis Conference, Why is Apomixis Important to Agriculture (1998).

Four modes of inheritance for apomixis have been proposed during the past 100 years: chromosomal non-homologies (wide hybridization), quantitative inheritance, simple inheritance, and complex inheritance. The chromosomal non-homology hypothesis, championed by A. Ernst, Bastardierung als Ursache der Apogamie im Pflanzenreich (Fischer, Jena 1918), states that apomixis is a function of chromosomal nonhomology and is one of several cytogenetic anomalies caused by wide hybridization. According to this theory apomixis is not controlled by genes directly, but is a consequence of divergence in chromosome structure. This hypothesis is no longer considered valid mainly because apomixis occurs in plants whose chromosomes appear to be homologous. J. G. Carman, Asynchronous Expression of Duplicate Genes in Angiosperms May Cause Apomixis, Bispory, Tetraspory, and Polyembryony, 61 Biol. J. Linnean Soc. 51-94(1997).

The quantitative-mode-of-inheritance hypothesis is also considered to be invalid. In the mid 20th century, it was supported by Muntzing, who believed apomixis resulted from a delicate balance of few to many recessive genes, and Powers, who believed that recessive genes caused the three major components of apomixis: failure of meiosis, apomictic embryo sac formation, and parthenogenesis. Asker & Jerling.

During the past 40 years, most apomixis scientists, including Bashaw, Nogler, Savidan, Sherwood, and Harlan, have supported the simple inheritance hypothesis, i.e. that one or two dominant genes confer apomixis. Asker & Jerling. This conclusion initially appears well founded in that Mendelian analyses repeatedly produce simple inheritance segregation ratios, e.g. 1:1 apomictic to sexual progeny ratios are often produced in crosses made between sexual and apomictic plants. Y. Savidan, Apomixis: Genetics and Breeding, 18 Plant Breed. Rev. 13-86 (2000). However, despite years of effort, no apomixis gene has been identified or isolated.

In the late 1990s, the duplicate-gene asynchrony hypothesis or hybridization-derived floral asynchrony theory (hereinafter, "HFA theory") was proposed for the evolution of apomixis. J. G. Carman, 61 Biol. J. Linnean Soc. 51-94 (1997). It implies complex inheritance and is based on a synthesis of concepts from various fields of biology. According to this hypothesis, the mode of inheritance for apomixis is not simple; nor is it simply quantitative, at least not in the standard way of viewing quantitative inheritance. In contrast, it is complex and is best explained through a series of five tenets, which build upon each other. The first three tenets have been published, J. G. Carman, 61 Biol. J. Linnean Soc. 51-94 (1997), and are summarized below. The last two tenets comprise unpublished concepts novel to the present invention and are presented herein.

First, apomixis is a developmentally-disjunct hybrid phenotype. Apomixis is disjunct from, not intermediate to, its parental female reproductive phenotypes, which, for convenience, are labeled parental phenotypes A and B. Plants exhibiting phenotypes A or B undergo normal sexual reproduction. Phenotypic differences between A and B are detected cytoembryologically through state-of-the-art microscopy techniques. They are not casually observed, which is why they have not been described previously.

Second, parental phenotypes A and B are distinctly different from each other with regard to the time periods in which meiosis, embryo sac formation, and embryony occur relative to gross ovule development.

Third, parental phenotypes A and B are themselves quantitatively inherited. Hence, nearly obligate apomixis, where most ovules of a given plant produce functional apomictic embryo sacs, is expressed because of polygenic heterozygosity. In populations of agamic complexes (populations of interbreeding sexual and apomictic species), multiple alleles exist for many of the critical loci, i.e. the critical loci are polymorphic. The polygenic heterozygosity responsible for nearly obligate apomixis involves specifically divergent alleles, which are maintained in natural populations because of natural selection. In contrast, facultative apomixis, where sexual and apomictic seeds commonly develop on the same plant, occurs when some of the more critical loci required for obligate apomixis become homozygous (or acquire alleles that encode similar schedules of ovule development) through genetic segregation.

Based on the HFA theory, efficient procedures for synthesizing facultatively apomictic plants from sexual plants have been described. J. G. Carman, Methods for Producing Apomictic Plants, WO 98/33374 (1998) (hereby incorporated by reference). These methods are used to produce highly apomictic plants that may or may not be genetically stable as defined above. The solution offered in WO 98/33374 is to produce highly apomictic plants, i.e. to reduce, as far as possible, the occurrence of sexual seed formation in apomictic hybrids by identifying or producing (through breeding) pairs of parent lines that are appropriately divergent in their female reproductive schedules such that facultative sexual development is minimized in the facultatively apomictic hybrid progeny. Synthetic apomicts produced in this manner may be used as apomictic hybrid lines for several to many generations before the harvested seed becomes useless for replanting due to serious contamination from seeds of sexual revertants. The contaminating revertant seeds are products of genetic segregation, and their presence degrades agronomic value. This situation would be analogous to the mixing of inferior $F_2$ and later generations of seed with elite $F_1$ hybrid seed in a conventional hybrid seed production program. The result would be an agronomically inferior product. WO 98/33374 did not address the subject of stabilization and control of apomixis. Hence, methods for modifying an apomict once it is synthesized were not provided.

In view of the above, it would be advantageous to provide methods that permit development of apomictic lines that are obligate, obligate unless induced to be facultative, or facultative unless induced to be obligate. By inducing facultative apomixis, the apomictic line can be improved, by conventional breeding strategies, and subsequently returned to the obligately apomictic condition for many years of field production. It should be appreciated that these and other advantages of the present application (discussed below) represent major advancements in the state-of-the-art.

SUMMARY OF THE INVENTION

It is an object of the present invention to provide a new breeding system that confers, stabilizes, and controls apomixis for the purpose of simplifying hybrid seed production such that all angiospermous crops can be used as hybrids.

It is also an object of the present invention to provide specialized plant breeding practices for successfully improving such apomicts.

It is another object of the present invention to provide methods that control apomixis by converting a facultative apomict, which has or has not previously been improved by plant breeding or genetic engineering procedures, to an obligate apomict, thus assuring perpetuation of its genotypic and phenotypic characteristics.

It is an object of the present invention to provide methods for creating apomictic plants from sexual plants without using mutagenic procedures or plants that are already apomictic. The present invention provides methods for producing apomictic plants from two or more sexual plants of the same or related species. One step of the method involves obtaining two sexual lines whose female reproductive phenotypes differ such that under the same environmental conditions (day length, light intensities, temperature regimes, etc.) an appropriate degree of asynchrony in female developmental schedules between the two lines occurs. Appropriate degrees of asynchrony include but are not limited to situations in which megasporogenesis in one line is initiated at about the same time embryo sac formation is initiated in the other line relative to the development of nongametophytic ovule and ovary tissues (nucellus, integuments, pericarp, etc) and other phenological factors such as photoperiod-regulated floral induction times. The accelerated line (line undergoing embryo sac development) would have already accomplished floral induction and megasporogenesis.

These and other objects can be addressed by providing a method for synthesizing genetically stable apomictic plants comprising:

(a) producing specifically through interracial or interspecific hybridization a diploid or polyploid plant that exhibits apomixis because of hybridization-derived floral asynchrony as previously detailed in WO 98/33374;

(b) producing through chromosome doubling or $B_{III}$ hybridization a polyploid derivative line from said apomictic plant such that duplicate genes responsible for apomixis are isolated from each other on opposite homeologous (interspecific) genomes such that recombination is suppressed among homeologous genomes within the polyploid derivative line; or (c) producing through chromosome doubling or $B_{III}$ hybridization a polyploid derivative line from said apomictic plant such that duplicate genes responsible for apomixis are isolated from each other by segmental allopolyploidy, with interracially-divergent genomes, and increasing fertility of said apomictic segmental allopolyploid by selfing or hybridizing with a similar plant to obtain sexually-derived progeny that express, because of fortuitous recombinations, greater pollen fertility, unreduced embryo sac formation, unreduced egg fertility, or parthenogenesis; or (d) producing through mutation or other plant stresses a derivative line of said apomictic plant that contains one or more chromosomal aberrations that isolate the duplicate genes responsible for apomixis from recombination during meiosis in the derivative line; or (e) transforming said apomictic plant with a recombinant DNA characterized by a promoter/gene construct that causes female meiosis to abort.

Another preferred embodiment of the invention relates to a method for genetically stabilizing a natural or synthetically produced apomictic plant exhibiting genetic instability comprising:

(a) producing through chromosome doubling or $B_{III}$ hybridization a polyploid derivative line from said plant such that duplicate genes responsible for apomixis are isolated from each other on opposite homeologous genomes such that recombination is suppressed among homeologous genomes within the polyploid derivative line; or (b) producing through chromosome doubling or $B_{III}$ hybridization a polyploid derivative line from said plant such that duplicate genes responsible for apomixis are isolated from each other by segmental allopolyploidy and increasing fertility of said apomictic segmental allopolyploid by selfing or hybridizing with a similar plant to obtain sexually-derived progeny that express, because of fortuitous recombinations, greater pollen fertility, unreduced embryo sac formation, unreduced egg fertility, or parthenogenesis; or (c) producing through mutation or other plant stresses a derivative line of said plant that contains one or more chromosomal aberrations that isolate the duplicate genes responsible for apomixis from recombination during meiosis in the derivative line; or (d) transforming said plant with a recombinant DNA characterized by a promoter/gene construct that causes female meiosis to abort.

Another preferred embodiment of the invention relates to a method for genetically improving plants comprising:

(a) identifying or synthesizing an apomictic plant, determining if apomixis in said apomictic plant is genetically stable, and if said apomictic plant is unstable, then genetically stabilizing it to result in a genetically-stabilized derivative line;

(b) genetically enhancing said apomictic plant or genetically-stabilized derivative line, either of which is a facultative apomict, through plant breeding procedures where genetically divergent sexual or apomictic lines are hybridized with said apomictic plant or genetically-stabilized derivative line or through genetic engineering procedures using transgenic constructs;

(c) breeding or transforming said plant, genetically-stabilized derivative line, or genetically-enhanced derivative line to include genetic material such that:

(i) female meiosis aborts resulting in essentially 100% apomictic seed formation except in the optional case of an inducible down regulation of a transgenic promoter/gene construct, which gene construct causes meiotic abortion when expressed, such that facultative apomixis is expressed during which time said plant may be further enhanced genetically through plant breeding procedures; or (ii) facultative apomixis occurs except during an inducible up regulation of a transgenic promoter/gene construct that when expressed causes meiotic abortion resulting in essentially 100% apomictic seed formation during which time apomictic hybrid seed may be multiplied;

(d) transforming said plant, genetically-stabilized derivative line, or genetically-enhanced derivative line to include genetic material such that:

(i) high frequency sexual seed formation (>5%) occurs except in the optional case of an inducible down regulation of a transgenic promoter/gene construct, which gene construct enforces high frequency sexual embryo sac and seed formation when expressed, such that obligate to near obligate apomixis is expressed (<5% sexual seed formation) during which time apomictic hybrid seed may be multiplied; or (ii) obligate to near obligate apomixis occurs (<5% sexual seed formation) except during an inducible up regulation of a transgenic promoter/gene construct that when expressed causes high frequency sexual seed formation (>5%) during which time said plant may be further enhanced genetically through plant breeding procedures.

BRIEF DESCRIPTION OF THE DRAWINGS

FIG. 9 shows sexual megasporogenesis and sexual and diplosporous embryo sac development in a synthetically stabilized obligately-apomictic trispecific triploid *Tripsacum* hybrid produced from sexual diploids (*T. laxum/T. pilosum// T. zopilotense*). About 80% of pistils in the hybrid exhibit diplosporous embryo sac formation. The remaining pistils are abortive.

DETAILED DESCRIPTION OF THE PREFERRED EMBODIMENTS

Figure 1:
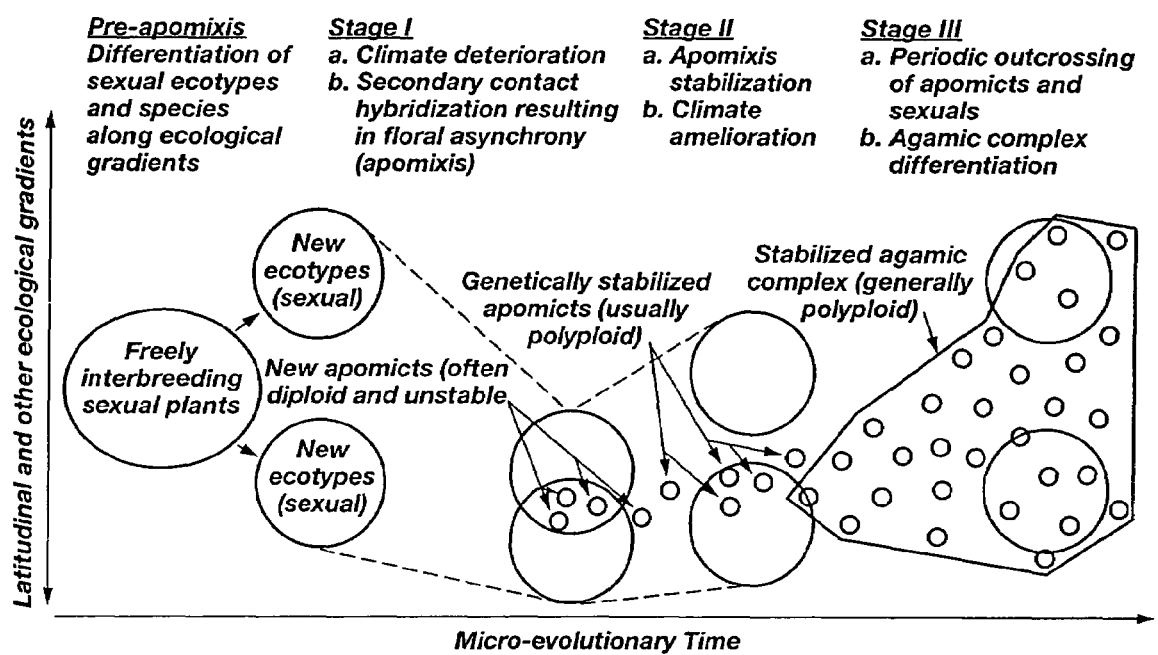
FIG. 1 shows stages in the evolution of agamic complexes. The stages include ecotypic differentiation prior to the formation of apomicts, formation of stage I apomicts through secondary contact hybridization, formation of stage II apomicts through structural (karyotypic) stabilization (usually involving polyploidization), and formation of mature, ecologically-diverse agamic complexes (stage III) through facultative outcrossing primarily with sexual relatives and secondarily with other related apomicts.

Before the present methods of stabilizing and controlling apomixis are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventor is not entitled to antedate such disclosure by virtue of prior invention.

It must be noted that, as used in this specification and the appended claims, the singular forms "a," "an," and "the" include plural referents unless the context clearly dictates otherwise.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

As used herein, "genetic instability" of an apomictic plant means the average frequency of sexual seed formation among sexually produced progeny of such plant exceeds that of such apomictic plant.

As used herein, "stabilizing" a facultatively apomictic plant means assuring that the average frequency of sexual seed formation among sexually derived progeny of such plant does not exceed that of such apomictic plant.

As used herein, "complete apomixis" means (1) preemption of megasporogenesis by precocious embryo sac formation, (2) preemption of fertilization by precocious embryony, and (3) formation of endosperm either pseudogamously (through fertilization of the central cell but not the egg) or autonomously (without fertilization of the central cell).

Tenets 4 and 5 of the HFA theory of apomixis are as follows:

Tenet 4 states that in the absence of structural or karyotypic heterozygosity, sexually produced progeny of a near obligate or facultative apomict generally reproduce sexually, that is, they are sexual revertants. In the absence of structural heterozygosity, the divergent alleles responsible for parental phenotypes segregate during sexual gamete formation, which in apomicts occurs rarely to frequently during megasporogenesis (female meiosis) and usually frequently during microsporogenesis (male meiosis). In this respect, loss of apomixis in the sexual $F_2$ generation is analogous to loss of hybrid vigor in the $F_2$ generation of standard hybrid varieties of crops. Both are complex polygenic hybrid phenotypes.

Tenet 5 states that in the presence of structural heterozygosity, sexually produced progeny of a near obligate or facultative apomict generally reproduce either apomictically, mimicking a homozygous dominant condition, or both sexually and apomictically (in a near 1:1 segregation ratio), mimicking a heterozygous dominant condition. In natural reproductively stabilized apomicts, high frequency segregation to sexuality is prevented by structural (karyotypic) heterozygosity, which includes, but is not limited to, allopolyploidy, segmental allopolyploidy, sexual sterility, or paleopolyploidy. Structural heterozygosity is responsible for apomixis mimicking simple inheritance.

Intraspecific apomictic diploid hybrids, whose sexual progeny are usually weakly apomictic or totally sexual due to recombination of the polygenic heterozygosity necessary for apomixis, are stabilized by inducing triploidy or other odd polyploid level. This results in near obligate apomixis. At the odd polyploid level, genetically-reduced and recombined functional eggs are seldom produced and seldom fertilized by genetically-reduced and recombined functional sperm, the production of which is greatly reduced. Hence, the intragenomic polygenic heterozygosity responsible for apomixis is seldom disturbed in odd polyploid apomicts.

Allopolyploidy (polyploidy involving different species) is generally the most convenient mechanism for restricting recombination. In an allopolyploid, recombination generally occurs only within genomes, not between genomes. Hence, genes responsible for apomixis are maintained, through facultative sexual generations, in a homozygous condition within genomes but a heterozygous condition between genomes.

Other cytogenetic mechanisms can be used to prevent recombination within or among whole genomes or only portions of genomes. This application extends to all such mechanisms including inversion or translocation heterozygosity and mechanisms of genetically controlled meiotic drive.

Fertility levels of interspecific apomictic diploids exhibiting low fertility are increased by polyploidization either at the even (e.g., tetraploid, hexaploid, and the like) or odd (e.g., triploid, pentaploid, and the like) levels. Apomictic polyploids produced in this manner may produce some sexually-derived progeny, i.e. they are generally facultative apomicts. Such sexually-derived progeny are also facultative apomicts because the polygenic heterozygosity required for apomixis exists between genomes not within genomes. Allopolyploidy fixes the responsible intergenomic heterozygosity such that occasional intragenomic recombination does not affect the allelic composition of the divergent intergenomic loci. Segmental allopolyploidization is encouraged by way of the methods of the present invention to enhance pollen fertility, unreduced embryo sac and egg production and viability, and unreduced egg parthenogenesis.

Development of HFA Theory

By combining HFA theory (all five tenets) with principles of evolutionary genetics, the present inventor developed a new theory for the origins, stabilization, and differentiation of natural "agamic complexes" (groups of interbreeding sexual and apomictic plants). The theory is presented herein and forms the basis for the production of "agamic crops."

During the pre-apomixis phase of the theory (FIG. 1), natural selection occurs along latitudinal and other ecological gradients, and sexual ecotypes with divergent spaciotemporal patterns of ovule development evolve. This is followed by secondary contact hybridization. In this context, the Pleistocene was unique in the history of angiosperms in that extensive plant migrations, B. Huntley & T. Webb III, Vegetation History (Kluwer Academic Publishers 1988), and secondary contact hybridizations occurred particularly in the mid-latitude heterogeneous refugial floras. J. G. Carman, 61 Biol. J. Linnean Soc. 51-94 (1997).

New hybrids attempting to express two or more specifically divergent spaciotemporal patterns of floral development reproduced as facultative stage I apomicts (FIG. 1). Most of these fledgling apomicts were diploid, and apomixis in most of them was facultative and transient, i.e. their sexually produced progeny were obligately sexual because the balanced multilocus heterozygosity required for apomixis had been disturbed by recombination. Hence, successive generations of these transient lines contained fewer apomicts until all apomicts were replaced by sexual progeny. Such replacement did not occur in apomicts that either possessed, at the time of their formation, or rapidly acquired stabilizing mechanisms such as allopolyploidy. Most mechanisms that stabilize apomixis involve polyploidy, and all of them greatly inhibit and sometimes eliminate recombination of the various heterozygous genes critical to apomixis and related reproductive anomalies.

Stabilized stage II apomicts may periodically engage in $B_{II}$ and $B_{III}$ hybridization with related apomicts and with ecologically-divergent sexual relatives to produce heterogeneous stage III agamic complexes (FIG. 1). Many stage III apomicts today continue to assimilate, through facultative outcrossing with sexual and apomictic relatives, the genetic capacity to migrate into new and ecologically diverse habitats. R. J. Bayer, Evolution of Polyploid Agamic Complexes with Examples from Antennaria (Asteraceae), 132 Opera Bot. 53-65 (1996).

The mechanisms for stabilizing the genetic inheritance systems responsible for apomixis complete the HFA model for the origins, stabilization, and inheritance of apomixis. With respect to apomixis, the component mechanisms (defined below) are not described in the prior art.

According to HFA theory, the parental sexual phenotypes of apomicts are polygenic coadaptations, A. R. Templeton, Coadaptation and Outbreeding Depression, in M. E. Soule, Conservation Biology: The Science of Scarcity and Diversity 105-116 (Sinauer Assocs. Inc., Sunderland, Mass. 1986); B. Wallace, Coadaptation Revisited, 82 J. Hered. 89-95 (1991), encoded by unique groupings of alleles that function cooperatively to confer fitness to specific ecotypes adapted to specific environments. Any significant recombination between parental genomes, i.e. between this critical multilocus heterozygosity in facultative stage I apomicts, results in progeny that display sexuality or, at best, a greatly reduced frequency of apomixis, i.e. the sexually produced progeny are sexual or mostly sexual (highly facultative). Hence, without stabilization, stage I apomicts are eventually replaced by sexual segregants that generally contribute only sexual progeny to the population.

The vast majority of diploid stage I apomicts that successfully progress to stage II (FIG. 1) are stabilized by allopolyploidy or segmental allopolyploidy. The rate at which stabilization occurs depends on the relatedness of the parental lines and on certain conditions in the secondary contact hybridization zone. One parental line, in such zones, is usually more common than the other. In such cases, pollen from the predominant parent is more likely to be involved in $B_{III}$ hybridizations (fertilization of unreduced eggs) to form triploids with a 2:1 genome ratio. Alternatively, the $B_{III}$ hybrid may be formed from unreduced pollen of the stage I apomict that affects fertilization of the predominant parent producing the same 2:1 genome ratio. Assuming the triploids also produce unreduced eggs (show tendencies for apomixis) or pollen, a second round of backcrossing involving the same predominant diploid sexual parent results in a 3:1 genome ratio. Such ratios are probably common among apomicts, and they explain simple inheritance segregation ratios and hemizygous apomixis-conferring linkage groups. Alternatively, the triploid may be involved in $B_{III}$ hybridization with the other parent, in which case a 2:2 genome ratio occurs. Other forms of polyploidization, involving unreduced pollen and eggs or somatic doubling, may produce similar results.

Most apomicts are outcrossing perennials, i.e. inbreeding apomicts and annual apomicts are extremely rare (Asker & Jerling). Mutation-based hypotheses fail to explain this observation. In contrast, the hybridization and outcrossing scheme described above (FIG. 1) depends on outcrossing and perenniality. At the diploid hybrid, $BC_1$ triploid, and $BC_2$ tetraploid levels, perenniality allows for numerous genetic recombinations (in pollen) to be tested. Each may provide a genetic background that confers a different degree of viability and facultativeness, and genetic backgrounds conferring higher viability survive.

Outcrossing and perenniality are characteristic of families with high rates of natural hybridization, and the Asteraceae, Poaceae, and Rosaceae frequently rank near the top. N. C. Ellstrand et al., Distribution of Spontaneous Plant Hybrids, 93 Proc. Nat=l Acad. Sci. USA 5090-5093 (1996). These three families contain 75% of all apomictic genera. J. G. Carman, 61 Biol. J. Linnean Soc. 51-94 (1997). In contrast, apomixis is seldom observed in families that rank low in hybridization rate, such as the Brassicaceae, Solonaceae, and Apiaceae. Again, while mutation-based hypotheses fail to explain these associations, they are wholly consistent with the hybridization and backcrossing origin described above (FIG. 1).

Because most apomicts are allopolyploids, Asker & Jerling, allopolyploidy is probably the most common form of apomixis stabilization. Recombination in true allopolyploids occurs within genomes only. Hence, loci critical to high frequency (near obligate) apomixis are isolated from intergenomic segregation and independent assortment, i.e. they remain homozygous within genomes but heterozygous across genomes. Progeny produced sexually from facultatively-apomictic TT T'T' genome allopolyploids, where T and T' are divergent and encode divergent patterns of ovule development, remain apomictic but are phenotypically variable because of within-genome recombination involving heterozygous loci not critical to apomixis.

When TTT T' apomicts reproduce sexually, the polygenic capacity for apomixis (from mostly sexual to nearly obligate) often segregates in a simple Mendelian manner. This occurs because it cosegregates with a nonrecombinant T' univalent (or large linkage group) that contains most of the more critical divergent alleles required for expression of a low to high frequency apomixis. It is likely that the many genes essential to a near obligate apomixis occur on several chromosomes. Hence, in crosses between TTTT sexual lines and TTT T' apomictic lines, facultativeness will vary from <10% to >90% among the segregants commonly classified as apomictic. Y. Savidan, Genetics and Utilization of Apomixis for the Improvement of Guineagrass (*Panicum maximum* Jacq), Proc XIV Int. Grassl. Congr., Lexington, K.Y., 1981, 182-184 (1983); S. Lutts et al., Male and Female Sporogenesis and Gametogenesis in Apomictic *Brachiaria brizantha*, *Brachiaria decumbes* and $F_1$ Hybrids with Sexual Colchicine Induced Tetraploid *Brachiaria ruziziensis*. 78 Euphytica 19-25 (1994). Such apomicts often approach 50% of the segregating population, i.e. a 1:1 segregation ratio is often approached, which is mistaken as evidence for simple inheritance. If the chromosome that contains most of the loci critical to apomixis assorts as a univalent, as is expected in a TTT T' genome constellation, it's transmission frequency will often fail to reach 50% due to microsatillite formation. This explains many segregation ratios that depict <50% apomixis transmission. Those adhering to the simple inheritance hypothesis explain this offset by tetrasomic inheritance with random chromatid assortment. Y. Savidan, Apomixis: Genetics and Breeding, 18 Plant Breed. Rev. 13-86 (2000).

Chromosome assortment in an apomixis-conferring homeologous TTT T' set occurs as if all four chromosomes are homologous. During meiosis, each of the three homologous T chromosomes has an equal chance of associating with its respective homeologous T' chromosome. Hence, if a locus common to all four chromosomes contains alleles that are different from each other, then all six pairwise combinations of the four different alleles will occur at random, i.e. the chromosome set mimics an autopolyploid.

In many apomicts, most of the polyploid chromosome sets behave genomically as autopolyploid sets, but at least one behaves as an allopolyploid set. This chromosome behavior is typical of segmental allopolyploidy. G. L. Stebbins Variation and Evolution in Plants (Columbia University Press, New York 1950); J. Sybenga, Chromosome Pairing Affinity and Quadrivalent Formation in Polyploids: Do Segmental Allopolyploids Exist?, 39 Genome 1176-1184 (1996). The allopolyploid set(s) maintains, across genomes, the balanced multilocus heterozygosity required for apomixis.

According to HFA theory, segmental allopolyploid apomicts evolve from early stage interracial autopolyploid or weakly allopolyploid TTT T' or TT T'T' apomicts. Recombination within the homeologous set(s) of chromosomes critical to apomixis is often nonadaptive because it usually results in sterile sexual segregants. Hence, allelic recombinations, chromosomal aberrations, or even mutations that inhibit recombination within the apomixis-conferring homeologous set cause a further allopolyploidization, G. L. Stebbins, Variation and Evolution in Plants (Columbia University Press, New York 1950), of this set, which may be highly adaptive resulting in the accumulation of such modifications. Likewise, recombinations within homeologous sets not strongly involved in conferring apomixis may also be highly adaptive. Such recombinations are initially infrequent, but with each additional recombination, similarity among chromosomes within homeologous sets increases, i.e. these cytogenetic events autopolyploidize chromosome sets by combining segments from divergent homeologous chromosomes into one chromosome. J. Sybenga, 39 Genome 1176-1184 (1996). Because such recombination does not result in sexual segregants, viability of the apomict incrementally increases by elimination of maladaptive allelic combinations present in the original hybrid and by the formation of new and adaptive allelic combinations. This mechanism may explain why apomicts in *Tripsacum*, D. Grimanelli et al., Mapping Diplosporous Apomixis in Tetraploid Tripsacum: One Gene or Several Genes?, 80 Heredity 33-39 (1998), D. Grimanelli et al., Non-Mendelian Transmission of Apomixis in Maize-Tripsacum Hybrids Caused by a Transmission Ratio Distortion, 80 Heredity 40-47 (1998), *Pennisetum*, P. Ozias-Akins et al., 95 Proc. Nat=l Acad. Sci. USA 5127-5132 (1998), *Cenchrus*, D. Roche, An Apospory-specific Genomic Region is Conserved Between Buffelgrass (*Cenchrus ciliaris* L.) and *Pennisetum squamulatum* Fresen, 19 Plant J. 203-208 (1999), and *Brachiaria*, S. C. Pessino et al., 130 Hereditas 1-11 (1999), behave genomically as autopolyploids yet fail to undergo recombination in the apomixis-conferring homeologous chromosome set or linkage group.

J. Sybenga, 39 Genome 1176-1184 (1996), argued persuasively that segmental allopolyploidy is eliminated by autopolyploidization early in the evolution of polyploids that originate as weak allopolyploids or interracial autopolyploids. The segmental allopolyploid apomict appears to be an exception. Herein, facultative apomixis coupled with segmental allopolyploidy are interdependent and highly adaptive traits, i.e. they function synergistically in the evolution and stabilization of mature highly successful agamic complexes (FIG. 1).

A few apparently-stable diploid apomicts exist in nature, and some of these are probably stabilized by near obligate sexual sterility, which prevents segregation. These may form either by interspecific hybridization of sexual diploids or from allopolyploid apomicts by parthenogenesis of reduced eggs. Examples include diploid apomicts in *Potentilla*, Muntzing & Muntzing, The Mode of Reproduction of Hybrids Between Sexual and Apomictic *Potentilla argentea*, 1945 Bot. Not. 49-71 (1945), *Hierochloe*, G. Weimarck, Apomixis and Sexuality in *Hierochloe australis* and in Swedish *H. odorata* on Different Polyploid Levels, 120 Bot. Not. 209-235 (1967), *Sorbus*, A. Jankun & M. Kovanda, Apomixis at the Diploid Level in *Sorbus eximia* (Embryological Studies in *Sorbus* 3), 60 Preslia, Praha 193-213 (1988), and *Arabis*, B. A. Roy, The Breeding Systems of Six Species of *Arabis* (Brassicaceae), 82 Amer. J. Bot. 869-877 (1995). In each case, genomes of the dihaploids are divergent, and sexual gametes seldom form.

In contrast, complete reversion to sexuality, within one to a few sexual generations, occurs in sexually-fertile diploid (or weakly dihaploid) apomicts. These unstable apomicts form either by interracial hybridization of sexual diploids or from segmental allopolyploid apomicts by parthenogenesis of reduced eggs. Note in the latter case that stabilized stage II or III polyploid apomicts may be parental to unstable stage I neodiploid apomicts (FIG. 1). Unstable apomictic diploids are found in *Parthenium*, D. U. Gerstel & W. M. Mishanec, On the Inheritance of Apomixis in *Parthenium argentatum*, 115 Bot. Gaz. 96-106 (1950), *Ranunculus*, G. A. Noger, 94 Bot. Hel. 411-422 (1984), and possibly *Themeda*, L. T. Evans & R. B. Knox, Environmental Control of Reproduction in *Themeda australis*, 17 Aust. J. Bot. 375-89 (1969), *Brachiaria*, T. N. Naumova et al., Apomixis and Sexuality in Diploid and Tetraploid Accessions of *Brachiaria decumbens*, 12 Sex. Plant Reprod. 43-52 (1999), and *Sorghum*, C. Y. Tang et al., Apomixis in *Sorghum* Lines and Their F1 Progenies, 141 Bot. Gaz. 294-299 (1980); U. R. Murty, Appraisal on the Present Status of Research on Apomixis in *Sorghum*, 64 Cur. Sci. 315-316 (1993), the latter of which appear to arise through hybridization of sexual diploids.

If apomixis were controlled by a single dominant gene, approximately 75% (if heterozygous) or 100% (if homozygous) of all sexually produced progeny of facultative diploid apomicts should be apomictic. However, such segregation ratios have never been observed. Instead, sexually produced progeny of facultative diploid apomicts are completely sexual or only weakly apomictic. These observations are inconsistent with simple inheritance, but they are wholly consistent with HFA theory, i.e. recombination of the balanced multilocus heterozygosity critical to apomixis generally results in sexual progeny. In short, at the diploid level, when slightly homeologous genomes facultatively recombine, apomixis is lost. At the polyploid level, homeology is sufficient to restrict facultative recombination to like genomes. This homeology mechanism maintains the cross-genome heterozygosity that often causes apomixis to appear to be simply inherited when apomicts are used as male parents in crosses between sexuals and apomicts.

As reviewed above, those endorsing the simple inheritance hypothesis explain 100% reversion to sexuality in sexually produced progeny of facultatively apomictic diploids by claiming that the dominant apomixis allele behaves as a recessive lethal in haploid gametes. Hence, according to this explanation apomixis cannot be inherited from the haploid gametes of diploid apomicts.

In addition to stabilizing certain diploid apomicts, sexual sterility provides added stabilization to polyploid and aneuploid apomicts. A few examples include (i) triploid apomicts in *Taraxacum*, Asker & Jerling, *Erigeron*, D. A. Stratton, Life History Variation Within Populations of an Asexual Plant, *Erigeron annuus* (Asteraceae), 78 Amer. J. Bot. 723-728 (1991), *Eupatorium*, M. S. Bertasso-Borges & J. R. Coleman, Embryology and Cytogenetics of *Eupatorium pauciflorum* and *E. intermedium* (Compositae), 21 Genet. Mol. Biol. 507-514 (1998), *Tripsacum*, C. A. Blakey et al., Co-segregation of DNA Markers with *Tripsacum* Fertility, 42 Maydica 363-369 (1997), *Paspalum*, B. L. Burson & M. A. Hussey, Cytology of *Paspalum malacophyllum* and its Relationship to *P. juergensii* and *P. dilatatum*, 159 Int. J. Plant Sci. 153-159 (1998), and *Cistanche*, B. Pazy, Diploidization Failure and Apomixis in Orobanchaceae, 128 Bot. J. Linn. Soc. 99-103 (1998), (ii) aneuploid apomicts in *Elymus*, J. B. Hair, Subsexual Reproduction in *Agropyron*, 10 Heredity 129-160 (1956), *Limonium*, J. A. Rossello et al., *Limonium carvalhoi* (Plumbaginaceae), a New Endemic Species from the Balearic Islands, 56 Anales Del Jardin Botanico De Madrid 23-31 (1998), *Tripsacum* and *Antennaria*, J. G. Carman, unpublished, and (iii) unequal tetraploid (three homologous x=5 genomes plus one homeologous x=4 genome) apomicts (nucellar embryony) in *Nothoscordum*, K. Jones, Robertsonian Fusion and Centric Fission in Karyotype Evolution of Higher Plants, 64 Bot. Rev. 273-289 (1998).

According to HFA theory, bispory, tetraspory and polyembryony are also polygenically-determined, anomalous, and developmentally-intermediate (hybrid) phenotypes. J. G. Carman, 61 Biol. J. Linnean Soc. 51-94 (1997). Like apomixis, they occur because of intergenomic heterozygosity for genes involved in the timing of megasporogenesis, embryo sac development, and/or embryony. However, unlike apomicts, many bisporic, tetrasporic and polyembryonic species are diploids, and nearly all bisporic and tetrasporic species are completely sexual. J. G. Carman, 61 Biol. J. Linnean Soc. 51-94 (1997). Hence, the multilocus heterozygosity critical to these anomalies is not stabilized by normal polyploidy, or by sexual sterility in the case of bisporic, tetrasporic, or facultatively polyembryonic diploids. This raises questions as to how such heterozygosity originated and how it is stabilized.

Bisporic and tetrasporic species, and many polyembryonic species, are paleopolyploids that appear to have formed from developmentally out-of-synchrony sexual or apomictic polyploids. J. G. Carman, 61 Biol. J. Linnean Soc. 51-94 (1997). Possible mechanisms of formation include ascending or descending aneuploidy and structural reorganizations of parental genomes. D. E. Soltis & P. S. Soltis, Polyploidy: Recurrent Formation and Genome Evolution, 14 Trends Eco. Evol. 348-352 (1999), both of which may be stabilized by diploidization. Without diploidization, segregation to normal monosporic Polygonum-type embryo sac formation would occur. Diploidization converts polyploid sets of homeologous chromosomes, in which recombination occasionally occurs, to recombinationally-distinct (diploidized) chromosomes, in which recombination among the newly distinguished and potentially reorganized diploid pairs never occurs. Hence, the ancestral multilocus intergenomic heterozygosity critical to bispory, tetraspory, and polyembryony is permanently stabilized through diploidization. Apomixis in certain diploid Arabis apomicts, and possibly a few other apomicts (diploid or polyploid), might also be permanently stabilized by diploidization.

The occurrence of extensive aneuploidy or grossly unbalanced chromosomal rearrangements prior to diploidization could make monospory (the norm) impossible for some bisporic and tetrasporic species and sexual embryo sac development impossible for some apomicts. However, cases of completely obligate bispory, tetraspory, and apomixis in plants are probably rare if they occur at all. H. Hjelmqvist, Variations in Embryo Sac Development, 14 Phytomorphology 186-196 (1964); Asker & Jerling; B. M. Johri et al., Comparative Embryology of Angiosperms, Vol. 1 and 2 (New York: Springer-Verlag 1992). In contrast, many unusual sexual and asexual reproductive systems of insects, amphibians, and reptiles are obligate. As with plants, most of these anomalous reproductive pathways are clearly associated with hybridization, polyploidy, diploidization, or other unusual cytogenetic mechanisms. E. Suomalainen et al., Cytology and Evolution in Parthenogenesis (CRC Press, Baca Raton, Fla. 1987). Hence, such mechanisms may also arise as polygenic hybrid phenotypes that are stabilized by normal or segmental allopolyploidy, sexual sterility, diploidization, or other cytogenetic mechanisms that prevent recombination of the multilocus heterozygosity critical to their maintenance.

The type of stabilization mechanism differentially affects heterosis and gene flow. For example, allopolyploidy of the form TT T'T' instantaneously stabilizes apomixis, but, barring mutations and infrequent outcrossing, few mechanisms exist for improving the fertility of such apomicts by modifying the original coadapted ovule-development programs. In contrast, potentially effective mechanisms for genome modification exist among segmental allopolyploid apomicts. In such apomicts, recombinational mixing occurs within those homeologous chromosome sets not directly involved in conferring apomixis, which probably includes the majority. Recombinations within these sets may enhance sexual pollen development, asexual egg development, parthenogenesis of unreduced eggs, and heterosis. In this sense, apomicts originating as inter-racial autopolyploids or weakly interspecific hybrids may rapidly acquire, through natural selection and autopolyploidization of nonapomixis-conferring chromosome sets, recombinations that confer high seed sets and high pollen fertility. Intergenomic recombinations deleterious to female sexuality reinforce selection against sexual revertants. Some intergenomic recombinations may cause the duplication or deletion of certain ovule development steps as seen in bispory and tetraspory. In this respect, apomixis may serve as an evolutionary springboard in the evolution of reproductively novel sexual species and genera including some that are bisporic, tetrasporic, or polyembryonic. J. G. Carman, 61 Biol. J. Linnean Soc. 51-94 (1997). In contrast, apomicts originating strictly as genomic allopolyploids, either TT T'T' or TTT T', may retain indefinitely many intergenomic heterozygosities not well adapted to apomixis.

Processes of the Present Invention

The present invention is directed to processes for producing genetically stabilized apomictic plants and genetically stabilizing natural or synthetically produced apomictic plants that exhibit genetic instability. It is also directed toward processes for controlling the expression of apomixis (facultativeness) for purposes of plant improvement, seed production, and crop production.

It is convenient to separate the processes of the present invention into four categories: (a) assessing genome homeology, facultativeness, and apomixis stability, (b) plant breeding, amphiploidization, and mutagenesis processes, (c) gene mapping and cloning processes, and (d) genetic engineering processes.

Assessing Genome Homeology, Facultativeness and Apomixis Stability

A feature of the present invention is the stabilization of apomixis in natural or synthetic apomicts by creating karyotypic (structural) heterozygosity. This is readily accomplished when apomicts are synthesized from sexual plants by choosing interspecific or interracial parental lines that also conform to the requirements of divergence in reproductive schedules of ovule development as taught in WO 98/33374. A preferred method of assessing the degree of karyotypic homeology of two sexual lines (being considered as hybridization pairs) involves conventional genome analyses where hybrids are produced and the extent of chromosome pairing is evaluated at metaphase I in pollen mother cells (PMC). D. R. Dewey, Genomic and Phylogenetic Relationships among North American Perennial Triticeae, in J. E. Estes et al., Grasses and Grasslands: Systematics and Ecology (University of Oklahoma Press 1982). At the diploid hybrid level, homeologous chromosome pairing in PMCs often greatly exceeds that observed when the diploid hybrid is amphiploidized. R. R-C. Wang, An assessment of genome analysis based on chromosome pairing in hybrids of perennial Triticeae, 32 Genome 179-189 (1989). Hence, diploid hybrids with even a limited degree of reduced chromosome pairing in PMCs may be appropriate for creating karyotypic heterozygosity by producing an amphiploid.

Facultativeness is a measure of the percentage of viable seeds that are formed sexually from an apomictic plant. A preferred method for determining this percentage is to conduct progeny tests in which the progeny are compared with the mother plant. Modern molecular fingerprinting techniques are preferred because of their reliability and ease of use once the systems are optimized. O. Leblanc & A. Mazzucato, Screening Procedures to Identity and Quantify Apomixis, in Y. Savidan & J. Carman, Advances in Apomixis Research (FAO, CIMMYT, ORSTOM, in press).

Degree of stability is assessed by conducting progeny tests on the off types identified in the first generation progeny tests. Progeny families whose members are apomictic like the mother plant come from a genetically stable (karyotypically heterozygous) apomictic mother. Progeny families whose members are represented by high percentages of sexual revertants come from genetically unstable apomicts. Typically, synthetic or natural diploid apomicts or natural dihaploid apomicts are unstable. Synthetic or natural polyploid apomicts may or may not be stable.

Plant Breeding, Amphiploidization and Mutagenesis

Conventional plant breeding procedures, as taught in standard plant breeding texts, e.g. Poehlman, Breeding Field Crops (Van Nostrand Reinhold 1987), are used for several purposes in the present invention. A preferred method is to increase genetic diversity and combining ability of sexual parental lines known to produce apomictic diploids or polyploids. Plant breeding or genetic engineering are used to genetically modify two sets of delineated parent lines of a plant species or closely related group of plant species that are differentiated in their reproductive phenotype such that hybridizing any plant from one of the two sets of delineated lines with any plant from the other set of delineated lines produces an apomictic plant or a plant that becomes apomictic through amphiploidization or further hybridization. Combining ability of parent lines is improved by standard crossing and inbreeding procedures or by single cross, double cross, or multi cross (outcrossing) procedures that are conducted within each set of delineated lines.

A feature of the present invention is the delineation of a new hybrid breeding system by which synthetically-derived hybrid apomicts are obtained. The system involves not only the identification of sexual inbred parent lines, which express good combining ability, but the identification of hybrid or multiply-outcrossed parental lines within the two sets of delineated lines such that good combining ability is expressed when a plant from one of the two sets of delineated lines is hybridized with a plant from the other set of delineated lines. Thus, this new operational system produces single or multi-cross hybrids that are either apomictic or become apomictic through amphiploidization or further hybridization. By this means, many apomictic hybrid genotypes can be produced (from each cross). Furthermore, each individual genotype may be increased through apomictic seed formation for field testing and/or cultivar release. Consequently, an unlimited number of new apomictic genotypes is rapidly produced. This technique will greatly increase the genetic diversity of plants used for agriculture and greatly increase the ability of breeders to provide apomictic hybrid varieties specifically adapted to highly, moderately or marginally productive agricultural regions.

A feature of the present invention extends the standard definition of combining ability to include development of divergent but highly heterozygous sexual parent lines that when hybridized (or hybridized and amphiploidized) result in apomictic plants with superior hybrid vigor. The genetically heterogeneous apomictic progeny obtained from crosses involving heterozygous (outcrossed) parental lines (sexual or apomictic) are individually evaluated for agronomic desirability and selected for cultivar development. Likewise, a preferred method is to cross a facultatively apomictic plant with genetically divergent sexual or apomictic lines to produce derived lines with enhanced agronomic traits.

For amphiploidization, the chromosome numbers of hybrids are doubled using standard colchicine techniques, e.g., J. Torabinejad et al., Morphology and Genome Analyses of Interspecific Hybrids of *Elymus scabrus*, 29 Genome 150-55 (1987). Alternatively, recently developed tissue culture techniques may be used. O. Leblanc et al., Chromosome Doubling in *Tripsacum*: the Production of Artificial, Sexual Tetraploid Plants, 114 Plant Breed. 226-30 (1995); Cohen & Yao, In Vitro Chromosome Doubling of Nine *Zantedeschia* Cultivars, 47 Plant Cell Tiss. Org. Cult. 43-49 (1996); Chalak & Legave, Oryzalin Combined with Adventitious Regeneration for an Efficient Chromosome Doubling of Trihaploid Kiwifruit, 16 Plant Cell Rep. 97-100 (1996).

Partially amphiploid 2n+n ($B_{III}$) hybrids are often produced in low frequencies (0.5% to 3%) when interspecific $F_1$s are backcrossed, e.g. Z. W. Liu et al., 89 Theor. Appl. Genet. 599-605 (1994), and this frequency may be much higher if tendencies for apomixis (unreduced egg formation) exist in the hybrids as taught in O. Leblanc et al., Reproductive Behavior in Maize-*Tripsacum* Polyhaploid Plants: Implications for the Transfer of Apomixis into Maize, 87 J. Hered. 108-111 (1996). Thus, a preferred method for doubling chromosomes of intraspecific and interspecific hybrids is to use one or more of the colchicine (or other known spindle inhibitor chemical) treatment methods listed above. Likewise, a preferred method for doubling chromosomes of interspecific hybrids involves backcrossing to one of the sexual parents and counting chromosomes in root tips to determine partial amphiploidy (usually triploidy). This is followed by backcrossing to the other parent to obtain a full amphiploid, or to the same parent to obtain a partial amphiploid (three genomes from one parent and one genome from the other). Amphiploidization may precede or follow hybridization.

Conventional mutation breeding procedures, as taught in the open literature, e.g., Poehlman, Breeding Field Crops (Van Nostrand Reinhold 1987), are used to induce chromosome inversions or translocations that isolate from recombination chromosome regions that contain genes required for apomixis. Preferred methods include regeneration of chromosomally rearranged plants from plant tissue cultures, S. Jain et al., Somaclonal Variation and Induced Mutations in Crop Improvement, Current Plant Science and Biotechnology in Agriculture 32, (Kluwer Academic Publishers 1998), and the obtainment of chromosomally rearranged plants following ionizing radiation, P. K. Gupta, Mutation Breeding in Cereals and Legumes, in S. M. Jain et al., Current Plant Science and Biotechnology in Agriculture 32 (Kluwer Academic Publishers 1998).

Use of male sterile lines or emasculation procedures are desirable if the plants are not dioecious or self incompatible. Hybrids are produced between sexual varieties or lines that display appropriate degrees of divergence in photoperiod responses and female developmental schedules. Intraspecific hybrids are made using standard techniques as taught in plant breeding texts, e.g. Poehlman, Breeding Field Crops (1987). The successful production of interspecific or intergeneric hybrids may require hormone treatments to the florets and embryo rescue procedures as taught in recent references involving wide hybridization, e.g. Z. W. Liu et al., Hybrids and Backcross Progenies between Wheat (*Triticum aestivum* L.) and Apomictic Australian Wheatgrass [*Elymus rectisetus* (Nees in Lehm.) A. Löve & Connor]: Karyotypic and Genomic Analyses, 89 Theor. Appl. Genet. 599-605 (1994). Hybrids are verified by their intermediate phenotype.

Gene Mapping and Cloning

A feature of the present invention involves controlling facultativeness by modifying expression of quantitative trait loci (QTLs) important to facultative expression using antisense technology. A preferred method begins with QTL mapping of the divergent sexual parental reproductive phenotypes responsible for apomixis occurring in hybrids produced by crossing said phenotypes. The method involves producing an $F_2$ mapping population, consisting of sexually derived $F_2$ progeny of a facultative synthetic $F_1$ apomict produced by hybridizing the original reproductively-divergent parent lines, and identifying molecular markers that associate with each phenotype, e.g. A. W. Heusden et al., Three QTLs from *Lycopersicon peruvianum* Confer a High Level of Resistance to *Clavibacter michiganensis* ssp. *Michiganensis*, 99 Theor. Appl. Genet. 1068-1074 (1999). Important QTL(s) are then fine-mapped to a given chromosome using a large segregating population and yeast artificial chromosomes (YACs) encompassing the chromosomal region are isolated by using flanking markers. A cosmid clone is then produced containing the QTL and complementing cosmids are identified by transformation into the mutant. The QTL transcript is then identified by cDNA isolation using the complementing cosmids, e.g. H. Q. Ling et al., Map-based Cloning of Chloronerva, a Gene Involved in Iron Uptake of Higher Plants Encoding Nicotianamine Synthase, 96 Proc. Nat=l Acad. Sci. USA 7098-7103 (1999); E. S. Lagudah et al., Map-based Cloning of a Gene Sequence Encoding a Nucleotide-binding Domain and a Leucine-rich Region at the Cre3 Nematode Resistance Locus of Wheat, 40 Genome 659-665 (1997). Alternatively, bacterial artificial chromosomes (BACs), which have been easier to work with, may be used for map-based cloning. BAC libraries have been produced for many crop species, e.g. S. S. Woo et al., Construction and Characterization of a Bacterial Artificial Chromosome Library of *Sorghum bicolor*, 22 Nucleic Acids. Res. 4922-4931 (1994).

Genetic Engineering

A feature of the present invention is to control degree of facultativeness by controlling the expression of a QTL important to facultative expression. Another feature of the present invention is to permanently (or reversibly) convert facultative apomicts to obligate apomicts by controlling the expression of meiosis-specific genes.

The preferred method for accomplishing obligate apomixis is to breed or transform a facultatively apomictic plant such that it contains a genetic material that causes female meiosis to abort resulting in essentially 100% apomictic seed formation. The genetic material may be a meiotic mutant, introduced through breeding, or a transgenic promoter/gene construct that when expressed disrupts female meiosis. An inducible down regulation of the transgenic promoter/gene construct, which gene construct causes meiotic abortion when expressed, allows for facultative apomixis to occur. Alternatively, facultative apomixis may occur except during an inducible up regulation of the transgenic promoter/gene construct thus causing meiotic abortion and essentially 100% apomictic seed formation.

The promoter/gene construct may contain a promoter from the group of promoters that are expressed immediately before or during female meiosis and a gene construct that when expressed fatally disrupts meiosis, e.g., V. I. Klimyuk & J. D. G. Jones, AtDMC1, the *Arabidopsis* homologue of the yeast DMC1 gene: characterization, transposon-induced allelic variation and meiosis-associated expression, 11 Plant J. 1-14 (1997); PCT/GB97/03546. The transgenic material, which is normally cytotoxic to female meiocyte development, may be controlled by a suppressor molecule encoded by a gene that is controlled by a chemically inducible promoter, which may be a female-meiocyte-specific promoter, such that female fertility (facultativeness) is inducible in such apomict. The transgenic material may contain a gene from the group of sense or antisense genes that when expressed during meiosis fatally disrupts meiosis or is otherwise cytotoxic to the female meiocyte. Furthermore, the method for restoration of a low level of female sexuality in a transgenically-derived obligate apomict may involve expression of a suppressor by induction of the inducible promoter. Introduction of the transgenic material into the host plant may employ any available technique well known to those skilled in the art.

EXAMPLES

Some of the features of the present invention may be better appreciated by reference to specific examples. It should be understood that the following examples are illustrative in nature rather than restrictive, and they are meant to demonstrate the basic teachings and concepts of the present invention rather than to limit the invention. It is expected that one of ordinary skill in the art will be able to use the information contained in the examples and elsewhere herein to apply the present invention to situations not specifically described herein.

Example 1

Selection of Lines Appropriate for Synthesizing Stable Apomictic Plants

It is a feature of the present invention to provide procedures for selecting sexual lines within the primary, secondary or tertiary germplasm pools of a given crop for the purpose of synthesizing stable facultatively-apomictic plants (those that do not readily form sexual segregants) from sexual plants or unstable facultatively-apomictic plants. In this example, there are illustrated preferred procedures for use with plants from the subclass Dicotyledonae, namely sexual species from the genus *Antennaria*, and from the subclass Monocotyledonae, namely sexual species from the genera *Tripsacum* and *Sorghum*. It is expected that one of ordinary skill in the art could successfully apply these procedures to many other crops, such as rice, sugar beet, apple, cherry, potato, soybean and lettuce.

The presently preferred procedure of selecting appropriate sexual parent lines is to (a) identify, from the literature or field studies, natural ecotypes and unimproved land races of a given crop species and its closely related species that differ with regard to shade tolerance, latitude, photoperiod requirements for flowering, altitude, and moisture preferences, (b) cytoembryologically characterize physiologically and ecologically divergent lines by relating stages of megasporogenesis and embryo sac development to stages of integument and gross ovary development, (c) characterize and statistically analyze the cytoembryological differences among lines, and (d) choose lines that are divergent physiologically (e.g. photoperiodism), cytoembryologically, and taxonomically. In general, plants classified as different species, i.e. pairs of plants whose hybrids are sterile, should possess sufficient genome homeology to assure karyotypic heterozygosity once the hybrid produced between them is amphiploidized.

Figure 2:
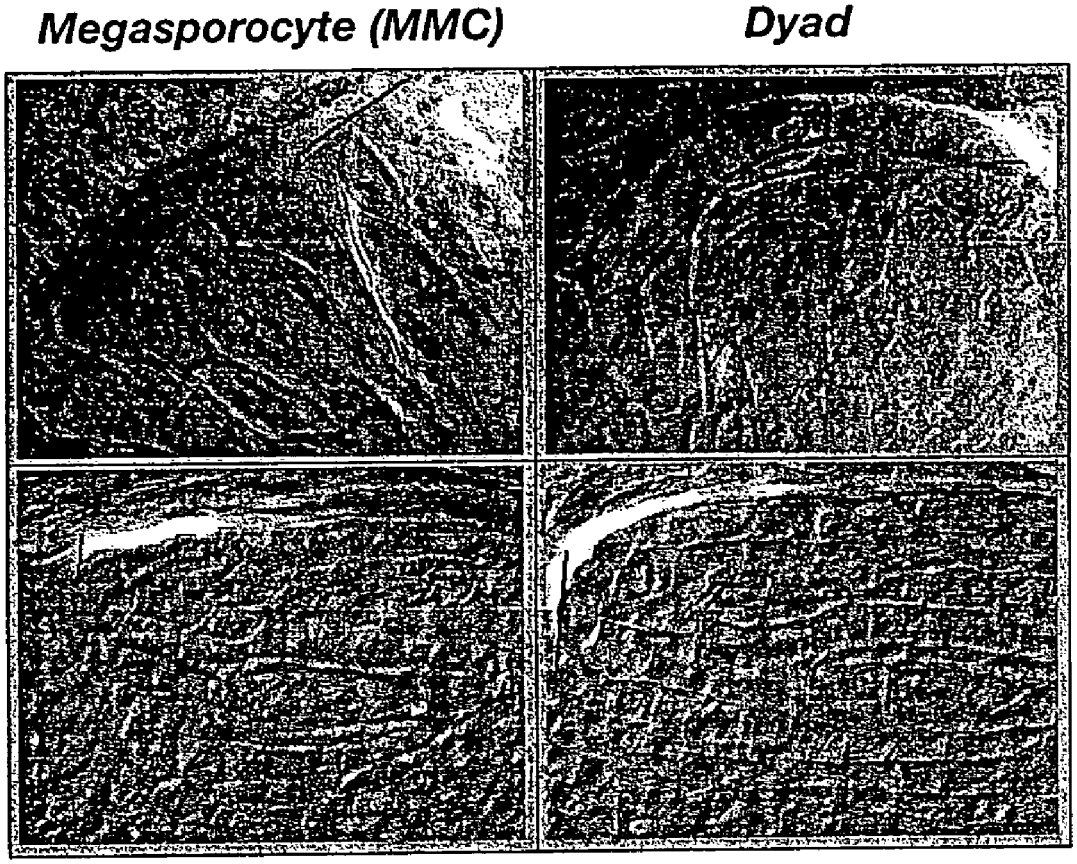
FIG. 2 shows megasporocyte (MMC) and dyad stages in pistils of sexual diploid *Antennaria racemosa* and *A. umbrinella*. Note integument length differences at the MMC and dyad stages between species. Arrows=MMC or dyad members. Lines=extent of integument growth. (Compare with FIG. 3).
Figure 3:
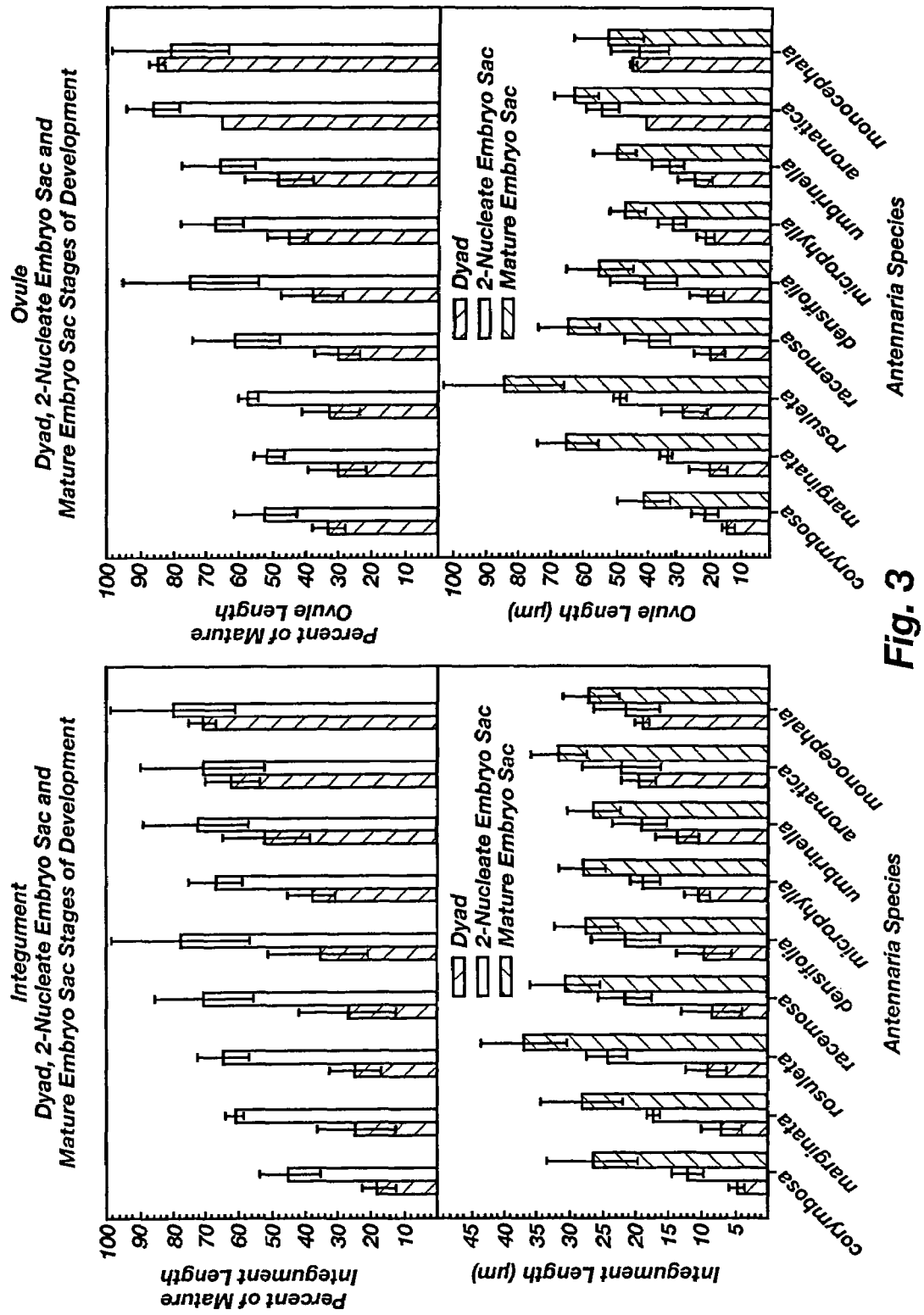
FIG. 3 shows mean integument and ovule lengths (actual measurements, bottom left and right, and as percentages of mature integument and ovule lengths, top left and right) at the dyad, 2-nucleate embryo sac, and mature embryo sac stages for nine diploid progenitors of apomictic *Antennaria rosea*. The data in FIGS. 8 through 11 depict variation, among plant ecotypes, in schedules of ovule development. This natural ecotypically-derived variation has never before been characterized, and it is a prerequisite for apomixis arising in nature and in synthetic hybrids.
Figure 4:
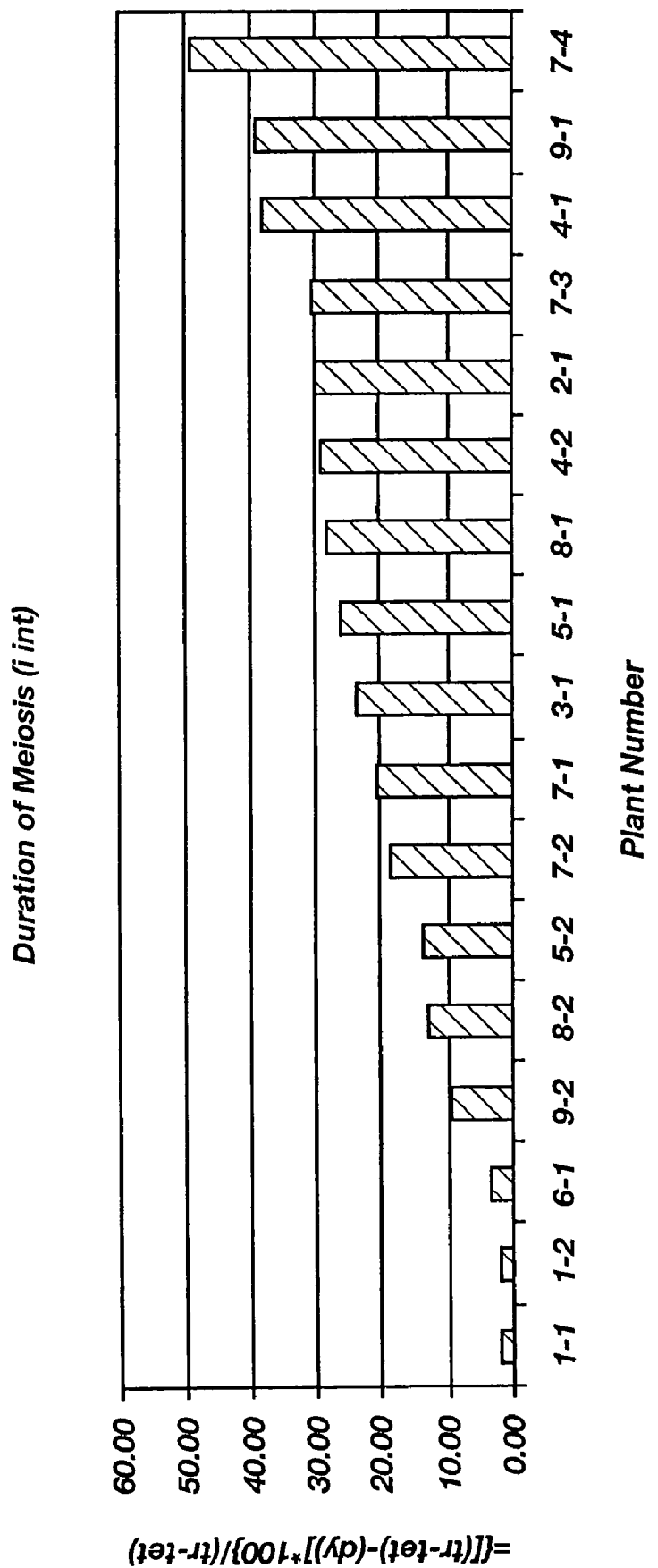
FIG. 4 shows one of several measures of duration of meiosis among 17 ecologically diverse *Sorghum* land races and varieties. Duration of meiosis is only one of several types of ecotypically-derived interracial/interspecific variation observed in the schedules of ovule development maintained by different ecotypes of flowering plants. The bars represent the duration of time between the dyad stage and the time in which embryo sac formation is initiated (as a function of inner integument growth), i.e. short and long bars represent lines with very little and much delay, respectively, between meiosis and embryo sac formation.
Figure 5:
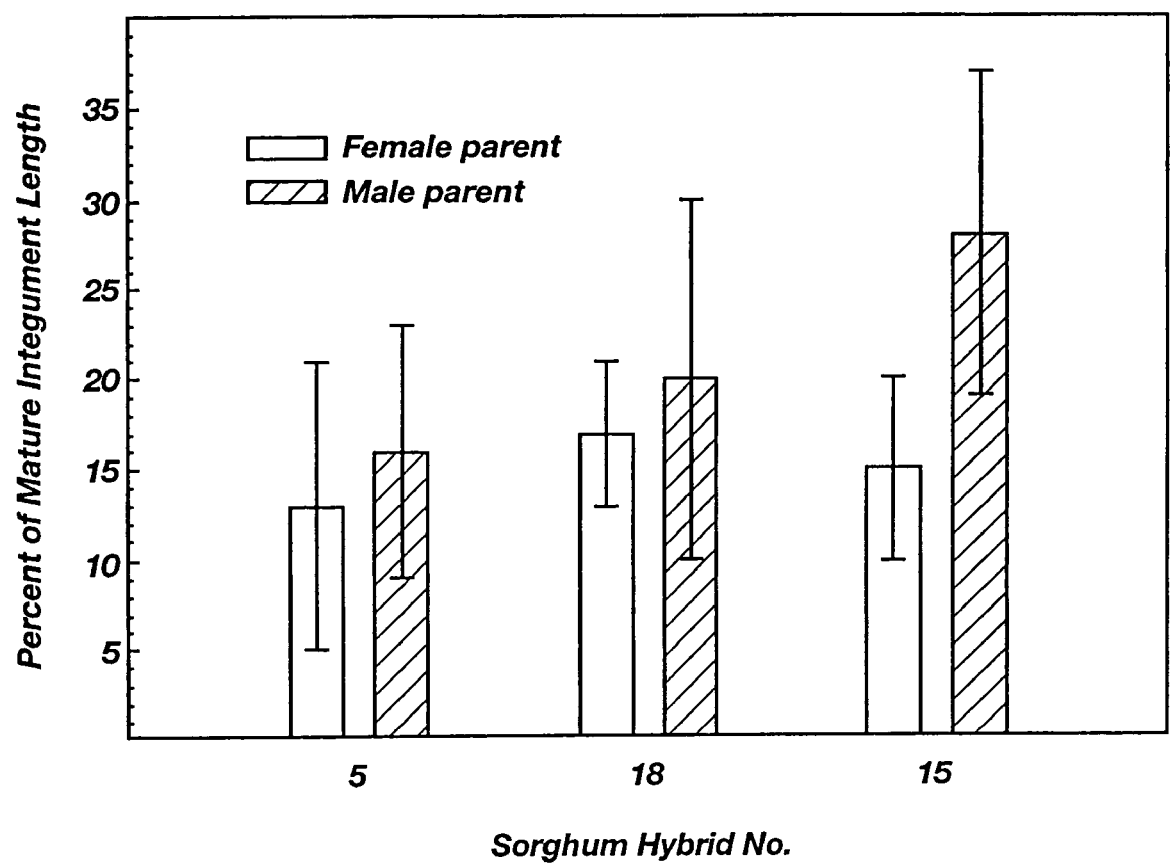
FIG. 5 shows flower bud maturity at the time of megasporogenesis (female meiosis) as measured by mean inner integument lengths (portrayed as percentages of mature integument lengths) at the dyad stage of meiosis for parent lines of three *Sorghum* hybrids. Aposporous initials and/or enlarging multinucleate apomictic (aposporous) embryo sacs are observed in about 5% of pistils from hybrids 5 and 18, whose parents show little difference in bud maturity levels at the time of megasporogenesis. In contrast, multinucleate apomictic (diplosporous) embryo sacs plus aposporous initials and embryo sacs form in about 10% of pistils from hybrid 15, whose parents show a much larger difference in bud maturity levels at the time of megasporogenesis. Apomictic embryo sac formation occurs only rarely (<0.1%) in the parent lines. Parent lines for hybrids 5, 18 and 15 are "Early Kalo"/"Karad Local", "Vir-5049"/"Aispuri" (converted), and "Westland"/ "Agira", respectively.

Sexual diploids and polyploids of *Antennaria, Tripsacum*, and *Sorghum* meet the geographical, physiological, ecological, cytoembryological and taxonomic criteria listed herein for synthesizing genetically-stable facultatively-apomictic plants from sexual plants. Ranging throughout the Rocky Mountain Cordillera, from the Arctic Circle region of the North West Territories, Canada, to the U.S. Mexico border, are numerous sexual *Antennaria* ssp. that collectively occupy a wide range of habitats but individually are often restricted to specific habitats. Bayer, 132 Opera Botanica 53-65 (1996). Significant differences in timing of meiosis relative to integument development are observed among these species (FIGS. 2 and 3). Ranging in the Americas from 42E N to 24E S latitude are numerous sexual *Tripsacum* ssp. that also collectively occupy a wide range of habitats but individually are often restricted to specific habitats. de Wet et al, Systematics of *Tripsacum dactyloides* (Gramineae), 69 Amer. J. Bot. 1251-57 (1982). Significant differences in timing of meiosis relative to integument development, similar to those observed among *Antennaria* spp., are also observed among these species (data not shown). Ranging throughout most of the African continent, Australasia and Southern Asia are numerous sexual diploid and polyploid ecotypes, landraces, and species of *Sorghum*. Significant differences in timing of meiosis relative to integument development are also observed among these species (FIGS. 4 and 5). Selection of appropriate sexual lines for synthesizing stable facultatively-apomictic plants can be made from these data. It will be appreciated that collection, characterization, and selection procedures are expected to vary somewhat with each monocotyledonous or dicotyledonous species.

Example 2

Synthesizing Genetically-stable Facultative and Obligate Apomicts

The techniques in Example 1 are used as guidelines to obtain three or more sexual lines with an early meiosis/early gametophyte development relative to development of the integument(s). The same techniques are used as guidelines to obtain three or more sexual lines of a closely related species with a late meiosis/late gametophyte development relative to development of the integument(s). The several lines of each category are selected such that embryo sac formation in one set of lines occurs at about the same time as prophase to early meiosis in the other set of lines relative to development of the integument(s). Pairs of parent plants (one plant from each of the two groups) are hybridized and amphiploids are produced using standard procedures described above. It will be appreciated that the genetic background in which the lines are derived may influence the expression of apomixis. Thus, selection or production of additional lines incorporating different genetic backgrounds and more or less divergence in timing of meiosis may be necessary.

Figure 6:
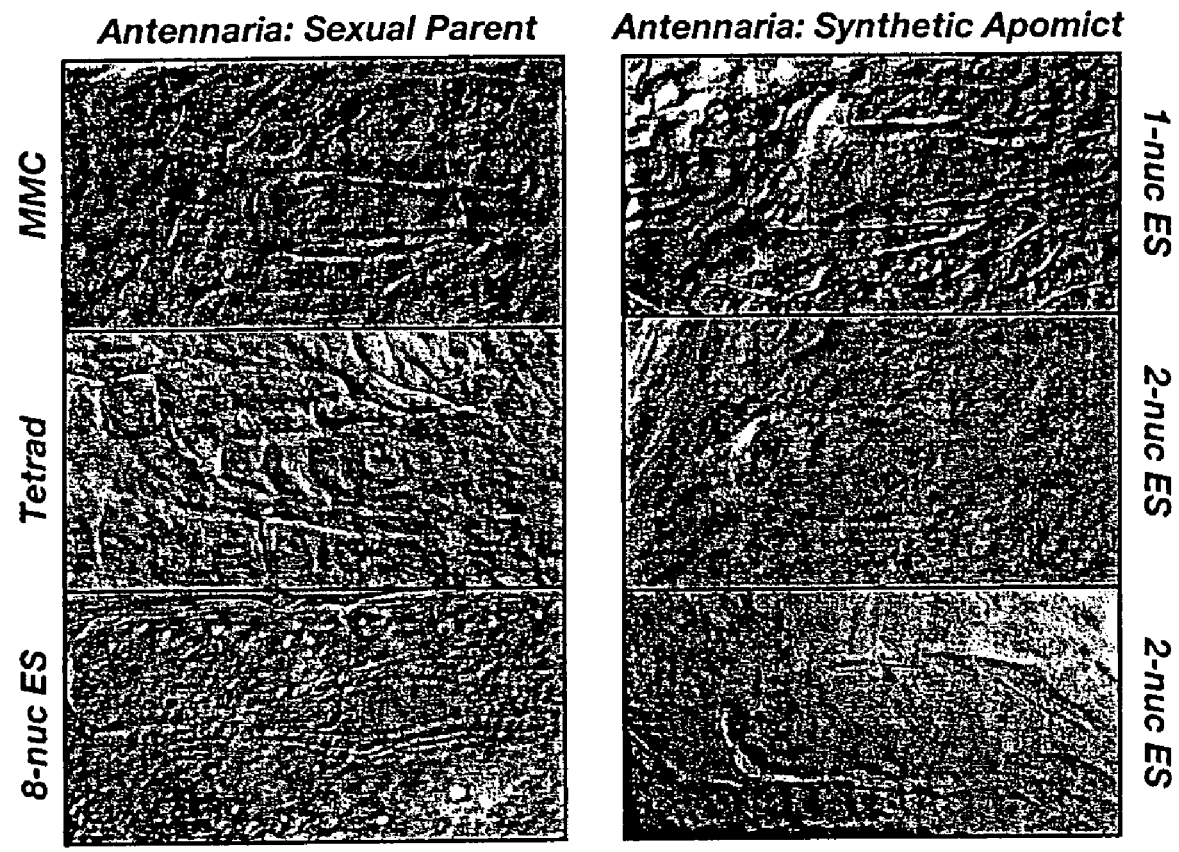
FIG. 6 shows megasporogenesis and embryo sac development in sexual *Antennaria* plus apomictic (diplosporous) embryo sac development in a synthetic *Antennaria corymbosa* (2n=2x, sexual)×*Antennaria racemosa* (2n=2x, sexual) interspecific apomictic hybrid. About 7% of pistils in the hybrid exhibit diplosporous embryo sac formation. Diplospory is not observed in the parent lines. Note from FIG. 3 that the two parent lines are not strongly divergent in timing of meiosis.
Figure 7:
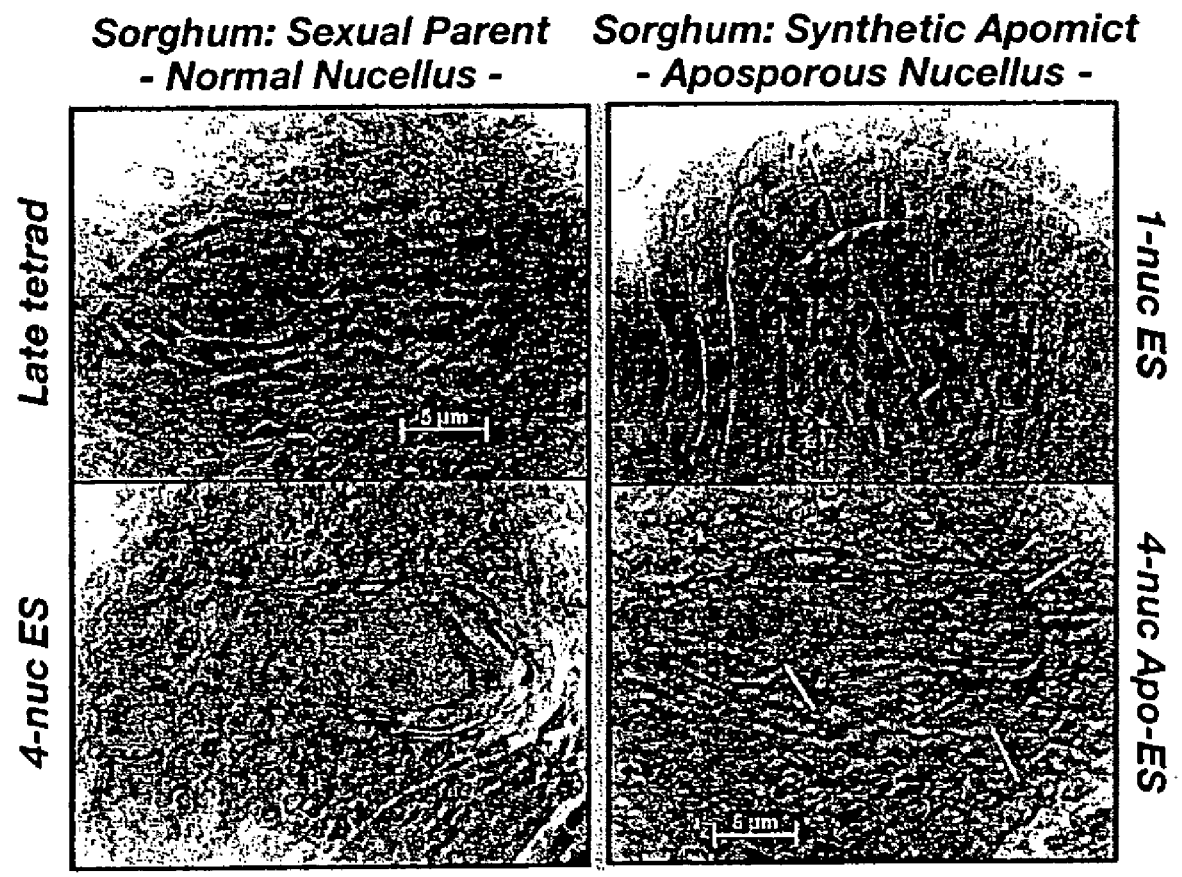
FIG. 7 shows megasporogenesis and embryo sac development in sexual *Sorghum* plus apomictic (aposporous) embryo sac development in a synthetic *Sorghum* hybrid produced from sexual lines. About 5% of pistils in the hybrid exhibit aposporous initials and/or aposporous embryo sac formation. Diplospory is not observed in the parent lines. Note from FIG. 3 that hybrids producing low frequency aposporous embryo sac formation are derived from parent lines that are not strongly divergent in timing of meiosis relative to overall bud development.

Facultative apomicts, which are unstable, meaning they produce sexual segregants as a result of facultative sexual reproduction, are synthesized as a result of hybridization-derived floral asynchrony by producing synthetic diploid *Antennaria corymbosa* (2x sexual)×*A. racemosa* (2x sexual) hybrids (FIG. 6) and synthetic diploid *Sorghum* (2x sexual) ssp. hybrids (FIG. 7). Aposporous embryo sacs form in *Sorghum* hybrids 5-1×4-1 and 9-1×1-2 at about a 5% frequency, and diplosporous embryo sacs, similar to those in *Tripsacum* (FIG. 8), form in *Sorghum* hybrids 5-2×9-2 at about a 10% frequency. Note that the divergence in timing of meiosis relative to integument development is substantial (FIG. 5) in the parental pairs whose progeny form diplosporous embryo sacs.

Structurally heterozygous (stable) facultative apomicts may be produced from the interspecific *Antennaria* and *Sorghum* $F_1$ hybrids by doubling their chromosome number using techniques discussed above. Stabilization of the intraspecific *Sorghum* hybrids (referred to above) requires a genetic modification that causes female meiosis or its immediate cell produces to abort, which not only stabilizes apomicts but makes them obligate. This is accomplished by incorporating a meiotic mutant into the line through standard hybridization procedures, by inducing triploidy through $B_{III}$ hybridization or amphiploidization followed by hybridization with a diploid, or by transforming the diploid with a promoter/gene construct that is cytotoxic to the female meiocyte using the methods discussed above. By using inducible promoters, as discussed above, genetically-stable apomicts with induced obligate or facultative expression may be produced.

Figure 8:
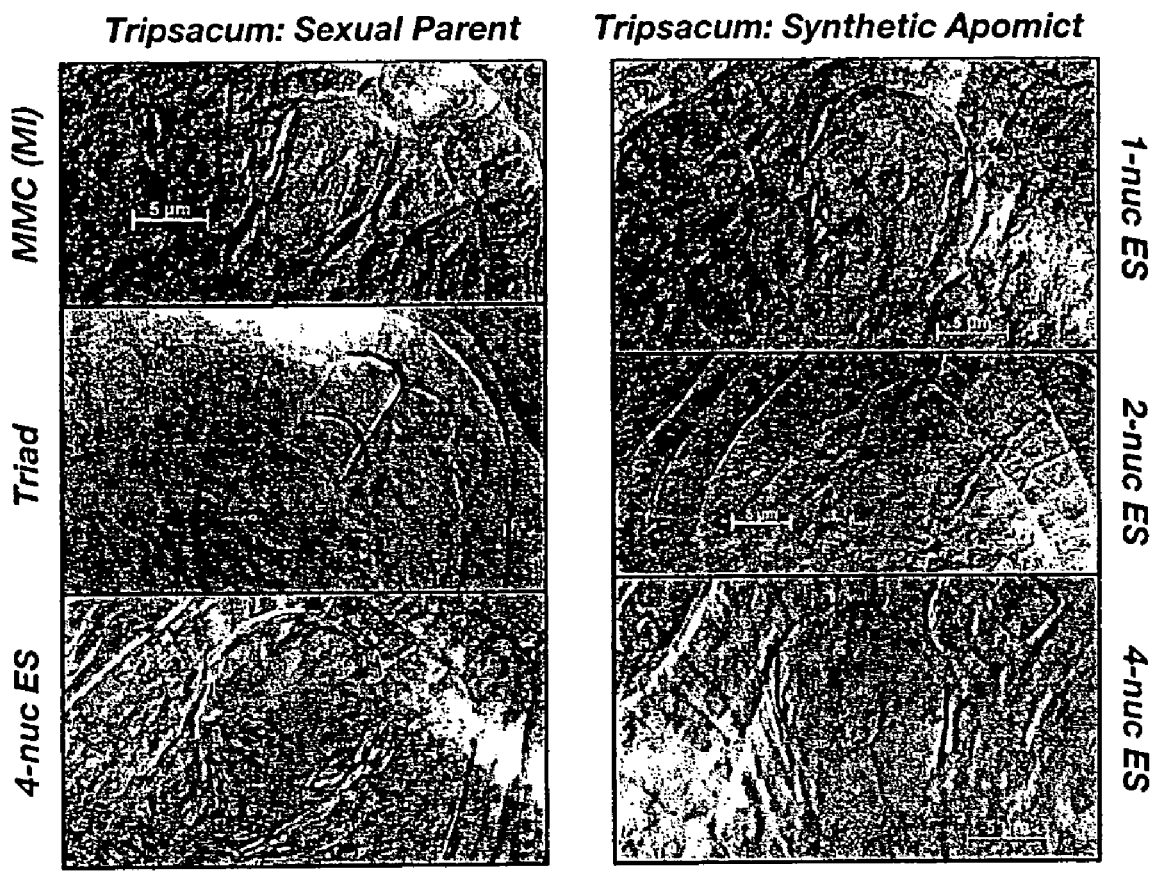
FIG. 8 shows sexual megasporogenesis and sexual and diplosporous embryo sac development in a synthetic facultatively-apomictic *Tripsacum* amphiploid (2n=4x) produced from the hybrid *T. laxum* (2n=2x, sexual)×*T. pilosum* (2n=2x, sexual). About 50% of pistils in the hybrid exhibit diplosporous embryo sac formation. Parthenogenic embryo formation from a reduced egg has been observed cytoembryologically (presence of a globular stage embryo with no fertilization of the central cell having yet occurred).

The synthetic amphiploid of diploid *Tripsacum laxum* (2x sexual)×*T. pilosum* (2x sexual) is a stable facultative apomict with 50% diplosporous embryo sac formation (FIG. 8). Crossing this plant with *T. zopilotense* (2x sexual) or *T. bravum* (2x sexual) produces stable obligate apomicts with about 80% diplosporous embryo sac formation and 20% abortive meiocyte or sexual embryo sac formation (FIG. 9).

Example 3

Mapping and Cloning Genes Responsible for Facultativeness

Genetic analyses of apomixis are conducted by pollinating sexual plants with the pollen from apomictic plants and scoring ovules in the progeny for sexual or apomictic development. It is common in these studies to score progeny as apomictic if any apomictically developing ovules are observed. For example, Y. Savidan, Nature et heredite de l=apomixie chez *Panicum maximum* Jacq., PhD thesis, Universite Paris XI, France (1982); S. Lutts et al., Male and female sporogenesis and gametogenesis in apomictic *Brachiaria brizantha, Brachiaria decumbes* and $F_1$ hybrids with sexual colchicine induced tetraploid *Brachiaria ruziziensis*, 78 Euphytica 19-25 (1994); C. B. Do Valle & J. W. Miles, Breeding of apomictic species, in Y. Savidan et al., Advances in Apomixis Research (2000); P. Ozias-Akins et al., 95 Proc. Nat=l Acad. Sci. USA 5127-5132 (1998), lumped plants into the apomixis category in which percentages of ovules developing apomictically were as low as 12, 28, 17, and 7%, respectively. What happened in these studies (whether it was intentional or not) was an identification of the minimal number of linkage groups required to encode at least some degree of functional apomixis. In some cases, gaps were observed among progeny in the percentage of ovules expressing apomixis, M. Dujardin & W. W. Hanna, Apomictic and sexual pearl millet×*Pennisetum squamulatum* hybrids, 74 J. Hered. 277-279 (1983), but in other cases the range of expression was somewhat continuous, S. Lutts et al., 78 Euphytica 19-25 (1994). Hence, it is believed that several major and perhaps many minor genes with quantitative effects (Y. Savidan, Nature et heredite de l=apomixie chez *Panicum maximum* Jacq., PhD thesis, Universite Paris XI, France (1982); S. Lutts et al., 78 Euphytica 19-25 (1994)) affect facultativeness (degree of apomixis expression).

It is a feature of the present invention to upregulate or down regulate facultativeness by modifying expression of QTL(s) using antisense technology. Using methods described above, QTL mapping is conducted for the divergent sexual parental reproductive phenotypes responsible for apomixis occurring in hybrids (FIGS. 2-5). Important QTL(s) are then fine-mapped to a given chromosome and identified as described above.

Example 4

Synthesizing Genetically-Stable Highly-Facultative Apomicts with Inducible Obligate Expression or Genetically-Stable Obligate Apomicts with Inducible Highly-Facultative Expression The techniques in Examples 1 through 3 are used as guidelines to synthesize genetically-stable highly-facultative apomicts with inducible obligate expression or genetically-stable obligate apomicts with inducible highly-facultative expression.

In the present invention, apomixis is analogous to a computer operating system. Features of this "biological operating system" include the following: (i) in farmers=fields, true-to-type "cloning" of hybrids from the hybrids=own seed—generation after generation, (ii) in plant breeders=nurseries, partial sexuality for plant improvement followed by reversion to strict apomixis, (iii) large numbers of rapidly-produced and genetically-diverse cultivars tailored to diverse agricultural niches, (iv) an increase in overall genetic diversity for protecting against widespread crop devastation by pests, and (v) a win-win reduction in expenses, i.e. farmers pay less for seed, and seed companies pay less to develop superior crop varieties.

Example 5

Quantifying Divergence in Female Developmental Schedules

It is a feature of the present invention to provide procedures for quantifying divergence among ecotypes in female developmental schedules. A presently preferred method, which is used with both dicotyledonous (e.g. *Antennaria*) and monocotyledonous (e.g., *Tripsacum*) plants, is to measure time intervals between floral bud formation, archespore formation, megasporogenesis, megagametogenesis, flowering, fertilization, and early embryo development (2 to 16 cell stage) using a combination of noninvasive measurements and destructive sampling. This information is obtained after the ecotypes chosen in Examples 1 and 2, i.e. those that represent latitudinal and other ecological extremes, have been grown in uniform conditions. Data gathered in Examples 3-5 are obtained simultaneously using the same sets of plants.

Cytological analyses of the female meiotic prophase, dyad, tetrad, and degenerating megaspore stages and the 1, 2, 4, and 8 nucleate embryo sac stages are conducted, and the following data are obtained for each ovule analyzed: meiotic or embryo sac development stage, pistil length and width, inner and outer integument lengths, and meiocyte or embryo sac length and width. Pistils for cytological analysis are killed, fixed, cleared, observed, and measured as in C. F. Crane & J. G. Carman (74 Amer. J. Bot. 477-96 (1987)), J. G. Carman et al., Comparative Histology of Cell Walls During Meiotic and Apomeiotic Megasporogenesis in Two Hexaploid Australian Elymus Species, 31 Crop Sci. 1527-32 (1991) (incorporated herein by reference); M. D. Peel et al., 37 Crop Sci. 724-32 (1997) (incorporated herein by reference); and M. D. Peel et al., Meiotic Anomalies in Hybrids Between Wheat and Apomictic Elymus rectisetus (Nees in Lehm.) A. Löve & Connor, 37 Crop Sci. 717-23, (1997) (incorporated herein by reference)). Developmental stage data are graphed against (a) pistil and integument lengths and widths (raw data) and (b) the lengths and widths of these structures represented as percentages of their mature lengths and widths (measured at stigma exsertion).

Example 6

Obtaining Greater Divergence in Female Developmental Schedules

It will be appreciated that sufficient divergence in (a) flowering responses to different photoperiods and (b) female developmental schedules will not be expressed among extant ecotypes of many cosmopolitan species even though sufficient genetic variability to establish such divergence by breeding may exist within their primary gene pools, i.e. within each cosmopolitan species as a whole. It is a feature of the present invention to provide breeding guidelines for increasing such divergence. As noted by D. Wilson, Breeding for Morphological and Physiological Traits, in K. J. Frey (ed), Plant Breeding II (Iowa State University Press, 1981) (incorporated herein by reference), many morphological and physiological traits, including flowering response to day length, are quantitatively inherited, which means they are influenced by many genes. Thus, much progress towards increasing the day length in which plants respond by flowering can be expected by intercrossing lines already showing some tendencies for this trait and selecting from among the progeny those lines that show greater tendencies. Much progress can be expected by repeating this process over several generations. In a similar manner, significant decreases in the day length in which plants respond by flowering can be expected by intercrossing lines already showing this tendency and following a similar regime of repeated selection and breeding. The traits for which it is presently preferred that divergence be maximized by such breeding schemes include (a) flowering responses to different photoperiods, i.e. producing long and short day ecotypes, and (b) accelerated and delayed initiations of archespore formation, meiosis, embryo sac development, etc, relative to the development of nongametophytic ovule and ovary tissues.

It will be understood that sufficient divergence in floral development will generally not be expressed among extant ecotypes of non-cosmopolitan species even though sufficient genetic variability to establish such divergence by breeding may exist within their secondary and tertiary gene pools, i.e. within the same genus, tribe, or family. It is contemplated that wide hybridization and even genetic engineering may in the future be used to incorporate into targeted species genes for (a) appropriate flowering responses and (b) appropriate divergence in female developmental schedules.

Example 7

Making Apomictic Plants from Sexual Lines Divergent in Floral Development

The techniques in Examples 1 through 6 are used as guidelines to obtain three or more lines of the same species (or closely related group of species) distinctly adapted to long days (14 to 20 h) and generally an early archespore development/early meiosis/early gametophyte development relative to the development of nongametophytic ovule and ovary tissues (nucellus, integuments, pericarp, etc). The same techniques are used as guidelines to obtain three or more lines of the same species (or group of species) distinctly adapted to short days (10 to 12 h) and generally a late archespore development/late meiosis/late gametophyte development relative to the development of nongametophytic ovule and ovary tissues. The several lines of each category (long-day plants and short-day plants, etc) are selected such that they form a continuum with regard to the day length in which flowering responses are induced, e.g. somewhat long, long, and very long and somewhat short, short, and very short. The lines are selected such that the initiation of embryo sac formation (degenerating megaspore stage) in one set of lines (usually the long-day-adapted lines) occurs at about the same time as female meiotic prophase through metaphase is occurring in the other set of lines relative to the development of the non-gametophytic tissues of the ovule and ovary.

Amphiploids are then produced using the standard procedures described above (colchicine induction or through repeated s production of B.sub.III hybrids) or other appropriate procedures. Standard hybridization procedures are used for producing hybrids among *Tripsacum* species. For Antennaria, pistillate plants are isolated by placing pollination bags (made from laboratory tissues, e.g. KTMWIPES) over the entire capitulescence. Pollination is accomplished by rubbing receptive pistillate inflorescences together with staminate heads at anthesis. Unpollinated control capitulescences are used to verify absence of apomixis of each parent clone. This is especially important with tetraploid clones in which either amphimictic or apomictic reproduction occurs. The pollination bags hold the fruits as they mature, and no embryo rescue is required.

At least three of the nine possible combinations of parents (one from each adaptation group) are made into amphiploids initially: the somewhat early line with the somewhat late line, the early line with the late line, and the very early line with the very late line. These are checked for the expression of apomixis as described above. Additional amphiploids from the nine possibilities are made if apomixis is not expressed. It will be appreciated that the genetic background in which the lines are derived may influence the expression of apomixis. Thus, the selection or production of additional lines incorporating different genetic backgrounds may occasionally be necessary.

It will be appreciated that the present invention may be embodied in other specific forms without departing from its spirit or essential characteristics, which reside in the discovery of the five tenets of the HFA theory. The described steps and materials are to be considered in all respects only as illustrative and not restrictive, and the scope of the invention is indicated by the appended claims rather than be the foregoing description. All changes which come within the meaning and range of equivalency of the claims are to be embraced within their scope.

What is claimed is:

1. A method of producing an angiospermous apomictic plant that exhibits an increased genetic stability for apomixis compared to an apomictic parent plant from which the apomictic plant is produced, the method comprising:
   (a) producing a facultatively apomictic parent plant by:
      selecting sexual plants from an angiospermous plant species, genus, or family;
      cytoembryologically ascertaining the developmental timing of the nongametophytic ovule and ovary tissues consisting of the nucellus, integument, pericarp, hypanthium, or pistil wall for each of the selected plants;
      choosing a first and a second plant based on the cytoembryologically ascertained developmental timing of the nongametophytic ovule and ovary tissues, wherein the initiation of embryo sac formation of the first plant is at the same time or before meiosis in the second plant;
      hybridizing the first plant with the second plant;
      recovering hybrid seed therefrom;
      sowing the hybrid seed; and
      selecting a hybrid plant that is apomictic to be the apomictic parent plant; and
   (b) doubling the chromosome number of the apomictic parent plant, thereby producing an angiospermous apomictic plant with increased genetic stability for apomixis.

2. The method of claim 1, wherein the step of doubling the chromosome number comprises treating the parent plant with a spindle inhibitor.

3. The method of claim 2, wherein the spindle inhibitor comprises colchicine.

4. The method of claim 1, wherein the step of doubling the chromosome number comprises culturing the parent plant in tissue culture.

5. The method of claim 1, wherein the step of doubling the chromosome number is accomplished by $B_{III}$ hybridization.

6. The method of claim 1, wherein the parent plant exhibits incomplete meiotic chromosome pairing such that meiotic chromosome pairing among the chromosomes of the resulting chromosome-doubled apomictic plant occurs within rather than among duplicated pairs of chromosomes.

7. The method of claim 1, wherein the parent plant is either an interspecific hybrid, so that the corresponding chromosome doubled plant is an allopolyploid, or an interracial hybrid, so that the corresponding chromosome doubled plant is a segmental allopolyploid.

8. The method of claim 1, further comprising the step of genetically modifying the apomictic plant to produce an apomictic plant in which female meiosis aborts.

9. The method of claim 8, wherein the step of genetically modifying the apomictic plant is accomplished by hybridization with a plant containing a meiotic mutant.

10. The method of claim 8, wherein the step of genetically modifying the apomictic plant is accomplished by hybridization with a plant of a different ploidy level so that the apomictic plant produced is of an odd ploidy level.

11. A method of producing an angiospermous apomictic plant that exhibits an increased genetic stability for apomixis compared to an apomictic parent plant from which the apomictic plant is produced, the method comprising:
   (a) producing a facultatively apomictic parent plant by:
      selecting sexual plants from an angiospermous plant species, genus, or family;
      cytoembryologically ascertaining the developmental timing of the nongametophytic ovule and ovary tissues consisting of the nucellus, integument, pericarp, hypanthium, or pistil wall for each of the selected plants;
      choosing a first and a second plant based on the cytoembryologically ascertained developmental timing of the nongametophytic ovule and ovary tissues, wherein the initiation of embryo sac formation of the first plant is at the same time or before meiosis in the second plant;
      hybridizing the first plant with the second plant;
      recovering hybrid seed therefrom;
      sowing the hybrid seed; and
      selecting a hybrid plant that is apomictic to be the apomictic parent plant; and
   (b) genetically modifying the apomictic parent plant so that female meiosis is aborted, thereby producing an angiospermous apomictic plant with increased genetic stability for apomixis.

12. The method of claim 11, wherein the step of genetically modifying the parent plant is accomplished by hybridization with a plant containing a meiotic mutant.

13. The method of claim 11, wherein the step of genetically modifying the parent plant is accomplished by hybridization with a plant of a different ploidy level so that the apomictic plant produced is of an odd ploidy level.

14. The method of claim 11, wherein the step of genetically modifying the parent plant is accomplished by $B_{III}$ hybridization.

15. The method of claim 11, wherein the step of genetically modifying the parent plant is accomplished by transforming the parent plant with a promoter/gene construct that inhibits female meiosis.

16. The method of claim 11, further comprising the step of doubling the chromosome number of the apomictic parent plant.

17. A method of producing a genetically stabilized angiospermous apomictic plant, the method comprising:
   cytoembryologically ascertaining the developmental timing of the nongametophytic ovule and ovary tissues of sexual plants, from an angiospermous plant species, genus, or family;
   choosing a first and a second sexual parent plant based on the cytoembryologically ascertained developmental timing of the nongametophytic ovule and ovary tissues of the sexual plants, wherein the initiation of embryo sac formation of the first plant is at the same time or before meiosis in the second plant;
   doubling the chromosome number of at least one of the sexual parent plants;
   hybridizing the first sexual parent plant with the second sexual parent plant to produce hybrid seed therefrom;
   sowing the hybrid seed; and
   selecting a hybrid plant that is an angiospermous apomictic plant with increased genetic stability for apomixis compared to the sexual parent plants.

18. The method of claim 17, wherein the step of doubling the chromosome number comprises treating the selected sexual plant with a spindle inhibitor.

19. The method of claim 18, wherein the spindle inhibitor comprises colchicine.

20. The method of claim 17, wherein the step of doubling the chromosome number comprises culturing the selected sexual plant in tissue culture.

21. The method of claim 17, wherein the step of doubling the chromosome number is accomplished by $B_{III}$ hybridization.

22. The method of claim 17, further comprising the step of genetically modifying the apomictic plant to produce an apomictic plant in which female meiosis aborts.

23. The method of claim 22, wherein the step of genetically modifying the apomictic plant is accomplished by hybridization with a plant containing a meiotic mutant.

24. The method of claim 22, wherein the step of genetically modifying the apomictic plant is accomplished by hybridization with a plant of a different ploidy level so that the apomictic plant produced is of an odd ploidy level.

25. The method of claim 1, wherein the sexual plants are selected from *Antennaria, Sorghum* or *Tripsacum*.

26. The method of claim 11, wherein the sexual plants are selected from *Antennaria, Sorghum* or *Tripsacum*.

27. The method of claim 17, wherein the sexual plants are selected from *Antennaria, Sorghum* or *Tripsacum*.

28. A method of producing an angiospermous apomictic plant that exhibits an increased genetic stability for apomixis compared to an apomictic parent plant from which the apomictic plant is produced, the method comprising:
(a) quantifying divergence in female developmental schedules of plants from an angiospermous plant species, genus, or family;
identifying and selecting a first and second sexual plant from an angiospermous plant species, genus, or family based on differences in the timing of female development schedules quantified in step (a), wherein the initiation time of embryo sac formation in the first plant occurs at about the same time as or before megasporogenesis in the second plant relative to the developmental maturity of the nongametophytic ovule and ovary tissues;
hybridizing the first plant and second plant;
recovering seed therefrom;
sowing the seed, and
selecting a hybrid plant that is apomictic; and
(b) doubling the chromosome number of the apomictic parent plant, thereby producing an angiospermous apomictic plant with increased genetic stability for apomixis.

29. The method of claim 28, wherein the step of quantifying divergence in female developmental schedules of plants including collecting data comprising the meiotic or embryo sac development stage, pistil length and width, inner and outer integument lengths, and meiocyte or embryo sac length and width; and the step of identifying and selecting a first and second sexual plants involves selecting plants such that a hybrid of the first and second sexual plant would result in asynchronous female development.

30. The method of claim 29, wherein the first plant and/or the second plant are obtained by plant breeding and the step of quantifying divergence in female developmental schedules includes comparing pistil and integument lengths and widths against the lengths and widths of the pistil and integument lengths at the mature lengths and widths at stigma exsertion.

31. The method of claim 28, wherein the step of quantifying divergence in female developmental schedules of plants includes at least two of the following: meiotic or embryo sac development stage, pistil length and width, inner and outer integument lengths, and meiocyte or embryo sac length and width.

32. The method of claim 28, wherein the step of quantifying divergence in female developmental schedules of plants includes producing data by screening plants within an angiospermous plant species, genus, or family for differences in the timing of initiation of megasporogenesis and embryo sac formation relative to the developmental maturity of nongametophytic ovule and ovary tissues among the plants including comparing pistil and integument lengths and widths against the lengths and widths of the pistil and integument lengths at the mature lengths and widths at stigma exsertion.

33. A method of producing an angiospermous apomictic plant that exhibits an increased genetic stability for apomixis compared to an apomictic parent plant from which the apomictic plant is produced, the method comprising:
(a) quantifying divergence in female developmental schedules of plants from an angiospermous plant species, genus, or family including cytologically analyzing the female meiotic prophase, dyad, tetrad, and degenerating megaspore stages, or nucleate embryo sac stages and collecting data including at least one of the following: meiotic or embryo sac development stage, pistil length and width, inner and outer integument lengths, and meiocyte or embryo sac length and width;
identifying and selecting a first and second sexual plant from an angiospermous plant species, genus, or family based on differences in the timing of female development schedules quantified in step (a), wherein the initiation time of embryo sac formation in the first plant occurs at about the same time as or before megasporogenesis in the second plant relative to the developmental maturity of the nongametophytic ovule and ovary tissues;
hybridizing the first plant and second plant;
recovering seed therefrom;
sowing the seed, and
selecting a hybrid plant that is apomictic; and
(b) doubling the chromosome number of the apomictic parent plant, thereby producing an angiospermous apomictic plant with increased genetic stability for apomixis.

\* \* \* \* \*